United States Patent
Blake-Haskins et al.

(10) Patent No.: US 10,556,009 B2
(45) Date of Patent: Feb. 11, 2020

(54) ANTI-BLYS ANTIBODY FORMULATIONS AND METHODS OF TREATMENT USING THEM

(71) Applicant: GlaxoSmithKline Intellectual Property Management Limited, Brentford, Middlesex (GB)

(72) Inventors: Angela Blake-Haskins, Gaithersburg, MD (US); Tristan Marshall, Gaithersburg, MD (US); Melissa D. Perkins, McPherson, KS (US); Kristin O'Berry, Gaithersburg, MD (US)

(73) Assignee: GlaxoSmithKline Intellectual Property Management Limited (GB)

( * ) Notice: Subject to any disclaimer, the term of this patent is extended or adjusted under 35 U.S.C. 154(b) by 0 days.

(21) Appl. No.: 15/311,223

(22) PCT Filed: May 15, 2015

(86) PCT No.: PCT/IB2015/053602
§ 371 (c)(1),
(2) Date: Nov. 15, 2016

(87) PCT Pub. No.: WO2015/173782
PCT Pub. Date: Nov. 19, 2015

(65) Prior Publication Data
US 2017/0095555 A1    Apr. 6, 2017

Related U.S. Application Data

(60) Provisional application No. 62/095,181, filed on Dec. 22, 2014, provisional application No. 62/093,734, filed on Dec. 18, 2014, provisional application No. 61/994,427, filed on May 16, 2014.

(51) Int. Cl.
| | |
|---|---|
| *A61K 39/395* | (2006.01) |
| *C07K 16/28* | (2006.01) |
| *C07K 16/24* | (2006.01) |
| *A61K 39/00* | (2006.01) |

(52) U.S. Cl.
CPC ...... *A61K 39/39591* (2013.01); *C07K 16/244* (2013.01); *C07K 16/2875* (2013.01); *A61K 2039/505* (2013.01); *C07K 2317/21* (2013.01); *C07K 2317/41* (2013.01)

(58) Field of Classification Search
None
See application file for complete search history.

(56) References Cited

U.S. PATENT DOCUMENTS

2007/0086979 A1*  4/2007  Chevrier .............. A61K 38/185
                                                                424/85.1

FOREIGN PATENT DOCUMENTS

WO   WO 2011/147921 A1   12/2011
WO   WO 2014/066468 A1    5/2014

OTHER PUBLICATIONS

Ghosh et al. Effect of arginine on protein aggregation studied by fluorescence correlation spectroscopy and other biophysical methods. Biochem. 48, 1135-1143, 2009. (Year: 2009).*
Pontarini et al., Treatment with belimumab restores B cell subsets and their expression of B cell activating factor receptor in patients with primary Sjogren's syndrome. Rheumatology 54, 1429-1434, 2015 (Year: 2015).*
Ahmed et al. Subcutaneous formulation of belimumab in treatment of systemic lupus erythematosus: a critical review with focus on safety and satisfaction. Patient Preference and Adherence. 12, 2475-2479, 2018. (Year: 2018).*
Wang, et al. Journal of Pharmaceutical Sciences, American Pharmaceutical Association, 96(1): 1-26 (Jan. 1, 2007).
Cai, et al. Clinical Pharmacology in Drug Development, 2(4): 349-357 (2013).
Shida, et al. Journal of Clinical Pharmacy and Therapeutics, 39(1):97-101 (2014).
April, et al. "Product Monograph BENLYSTA™". (Apr. 16, 2014). Originally retrieved from the Internet: URL:http://www.gsk.ca/english/docs-pdf/product-monographs/Benlysta.pdf.

* cited by examiner

*Primary Examiner* — Elly-Gerald Stoica
(74) *Attorney, Agent, or Firm* — Hao Yin

(57) ABSTRACT

The present invention relates to pharmaceutical formulations of a pharmaceutically active antigen binding protein, for example a monoclonal antibody. Such formulations comprise, in addition to the antigen binding protein, a buffering agent and a tonicity agent.

25 Claims, 20 Drawing Sheets
Specification includes a Sequence Listing.

Black- acetate
Grey- succinate
Light Grey- histidine

US 10,556,009 B2

ANTI-BLYS ANTIBODY FORMULATIONS AND METHODS OF TREATMENT USING THEM

This application is a § 371 of International Application No. PCT/IB2015/053602, filed 15 May 2015, which claims the benefit of U.S. Provisional Application Nos. 62/095,181, filed 22 Dec. 2014; 62/093,734, filed 18 Dec. 2014; and 61/994,427, filed 16 May 2014; which are incorporated herein in their entireties.

FIELD OF THE INVENTION

The present invention relates to pharmaceutical formulations of a pharmaceutically active antigen binding protein, for example a monoclonal antibody. Such formulations comprise, in addition to the antigen binding protein, a buffering agent and a tonicity agent.

BACKGROUND OF THE INVENTION

The pharmaceutical use of antibodies has increased over the past years. In many instances such antibodies are injected via the intravenous (IV) route. Unfortunately the amount of antibody that can be injected via the intravenous route is limited by the physico-chemical properties of the antibody, in particularly by its solubility and stability in a suitable liquid formulation and by the volume of the infusion fluid. Alternative administration pathways are subcutaneous or intramuscular injection, which offer potential advantages in terms of patient compliance and ease of administration. These injection pathways require high protein concentration in the final solution to be injected.

Accordingly, there is a desire to provide highly concentrated, stable pharmaceutical formulations of therapeutically active antigen binding proteins such as antibodies for subcutaneous injection. The advantage of subcutaneous injections is that it allows the medical practitioner to perform it in a rather short intervention with the patient. Moreover the patient can be trained to perform the subcutaneous injection by himself. Such self-administration is particularly useful during maintenance dosing because no hospital care is needed (reduced medical resource utilization). Usually injections via the subcutaneous route are limited to approximately 2 mL. For patients requiring multiple doses, several unit dose formulations can be injected at multiple sites of the body surface.

SUMMARY OF THE INVENTION

In one aspect the present invention provides a pharmaceutical formulation for an antigen binding protein comprising a buffering agent and a tonicity agent. More particularly, the present invention provides about 150 to 250 mg/mL antigen binding protein; about 1 to 100 mM of a buffering agent providing a pH of about 5.0 to about 7.0; and about 70 to 170 mM of a tonicity agent. In one embodiment the antigen binding protein is an anti-BLyS antibody.

In another aspect the present invention provides a pharmaceutical formulation for an antigen binding protein comprising a buffering agent, a stabilizer, a tonicity agent, and a nonionic surfactant. More particularly, the present invention provides a pharmaceutical formulation comprising the antigen binding protein, histidine, arginine, NaCl, and polysorbate 80. In one embodiment the antigen binding protein is an anti-BLyS antibody.

In another aspect the present invention provides for a method of treating a disease or condition which is amenable to treatment with an anti-BLyS antibody in a subject comprising administering a formulation according the present invention in a subject in an amount effective to treat the disease or condition. In one aspect the disease or condition is an autoimmune disease or disorder.

In another aspect the present invention provides for a kit comprising one or more vials containing the formulation according to the present invention and instructions for subcutaneous administration of the formulation to a patient.

In another aspect the present invention provides for an injection device comprising a stable anti-BLyS antibody formulation described herein.

In another aspect the present invention provides for a formulation according to the present invention for use in the treatment of disease selected from the group consisting of systemic lupus erythematosus, anti-neutrophil cytoplasmic antibody ("ANCA") vasculitis, lupus nephritis, primary Sjögren's syndrome, chronic immune thrombocytopenia, myasthenia gravis, symptomatic Waldenström's macroglobulinaemia, immune desensitizing of patients awaiting kidney transplant, membranous nephropathy, systemic sclerosis, rheumatoid arthritis, multiple myeloma, multiple sclerosis, and kidney failure.

DETAILED DESCRIPTION OF THE INVENTION

Figure 1:
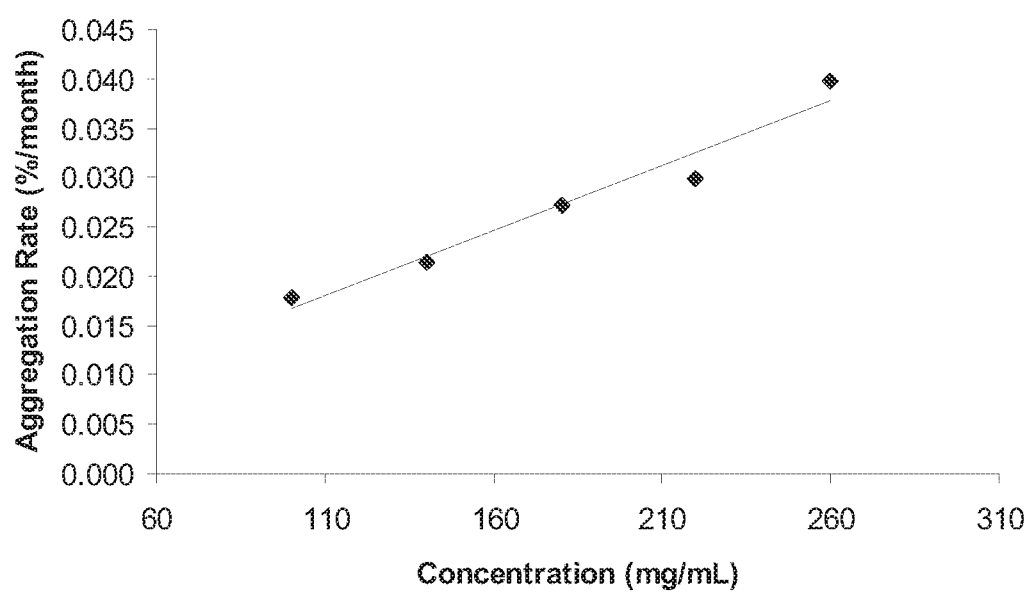
FIG. 1 shows the effect of protein concentration on aggregation rate for Formulation 1.

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a polypeptide" includes a combination of two or more polypeptides, and the like.

"About" as used herein when referring to a measurable value such as an amount, a temporal duration, and the like, is meant to encompass variations of ±20% or ±10%, including ±5%, ±1%, and ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

In one aspect the present invention provides a pharmaceutical formulation for an antigen binding protein comprising a buffering agent, and a tonicity agent. In another aspect the present invention provides a pharmaceutical formulation for an antigen binding protein comprising a buffering agent, a stabilizer, a tonicity agent, and a nonionic surfactant. In one embodiment the formulation is lyophilized or spray dried. In certain embodiments the formulation is lyophilized or spray dried and then later reconstituted with a dispersing agent. In one embodiment the dispersing agent is sterile water or "water for injection" (WFI). The antigen binding protein can be further diluted with isotonic saline or other excipients to produce a desirable concentration prior to administration. In one embodiment the formulation is a reconstituted formulation. In another embodiment the formulation is a liquid pharmaceutical formulation.

The term "pharmaceutical formulation" or "formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free from all living microorganisms and their spores.

In exemplary embodiments of the present invention, the liquid formulations exhibit desirable characteristics, such as desirable viscosity and surface tension characteristics.

The term "surface tension" refers to the attractive force exerted by the molecules below the surface upon those at the surface/air interface, resulting from the high molecular concentration of a liquid compared to the low molecular concentration of the gas. Liquids with low values of surface tension, such as nonpolar liquids, flow more readily than water. Typically, values of surface tensions are expressed in newtons/meters or dynes/centimeters.

"Dynamic surface tension" as referred to herein is the surface/air interface and the dynamic interfacial tension to the surface/surface interface. There are a number of alternative methods for measuring dynamic surface tension, for example, captive bubble surface tensionometry or pulsating bubble surface tensionometry.

The term "viscosity" refers to the internal resistance to flow exhibited by a fluid at a specified temperature, the ratio of shearing stress to rate of shear. A liquid has a viscosity of one poise if a force of 1 dyne/square centimeter causes two parallel liquid surfaces one square centimeter in area and one square centimeter apart to move past one another at a velocity of 1 cm/second. One poise equals one hundred centipoise.

In one embodiment, the viscosity of the formulation comprising buffering agent and stabilizer is reduced by at least about 5%, at least about 10%, at least about 15%, at least about 20%, at least about 25%, or at least about 30% compared to the viscosity of the formulation in the absence of buffering agent and stabilizer. In one embodiment, the viscosity of the formulation comprising buffering agent and stabilizer is less than about 50 cP, less than about 45 cP, less than about 40 cP, less than about 35 cP, less than about 30 cP, less than about 25 cP, less than about 20 cP, less than about 15 cP, or less than about 10 cP.

When referring to apparent viscosity, it is understood that the value of viscosity is dependent on the conditions under which the measurement was taken, such as temperature, the rate of shear and the shear stress employed. The apparent viscosity is defined as the ratio of the shear stress to the rate of shear applied. There are a number of alternative methods for measuring apparent viscosity. For example, viscosity can be tested by a suitable cone and plate, parallel plate or other type of viscometer or rheometer.

"Gelation is defined as the process of formation of a stiff network presumably caused by the onset of topological overlaps among polymerizing mAb or filaments as well as the cross-linking and bundling of these filaments. This stiff network manifests as a solution elastic modulus (G) as well as an increase in its inherent viscous modulus (G")."

In one aspect, the present invention is directed to a method of reducing or inhibiting gelation of a solution comprising utilizing a formulation of the present invention. In another aspect, the present invention is directed to a method of reducing or inhibiting gelation of a solution comprising a therapeutic protein, the method comprising administering histidine and sodium chloride to the solution.

"Polypeptide," "peptide" and "protein" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine: D- or L-phenylglycine; D- or L-2 thieneylalanine: D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine: D-(trifluoromethyl)-phenylglycine; D-(trifluoromethyl)-phenylalanine: D-p-fluorophenylalanine: D- or L-p-biphenylphenylalanine; K- or L-p-methoxy-biphenylphenylalanine: D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. The biological activity of the peptides can be determined by standard methods known to those of skill in the art and described herein.

"Recombinant" when used with reference to a protein indicates that the protein has been modified by the introduction of a heterologous nucleic acid or protein or the alteration of a native nucleic acid or protein.

As used herein a "therapeutic protein" refers to any protein and/or polypeptide that can be administered to a mammal to elicit a biological or medical response of a tissue, system, animal or human that is being sought, for instance, by a researcher or clinician. A therapeutic protein may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

All "amino acid" residues identified herein are in the natural L-configuration. In keeping with standard polypeptide nomenclature, abbreviations for amino acid residues are as shown in the following table.

TABLE 1

Amino acid abbreviations.

| 1 Letter | 3 Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine. |

It should be noted that all amino acid residue sequences are represented herein by formulae whose left to right orientation is in the conventional direction of amino-terminus to carboxy-terminus.

In another embodiment the polypeptide is an antigen binding protein. In one embodiment the antigen binding protein is selected from the group consisting of a soluble receptor, antibody, antibody fragment, immunoglobulin single variable domain, Fab, F(ab')2, Fv, disulphide linked Fv, scFv, closed conformation multispecific antibody, disulphide-linked scFv, or diabody.

The term "antigen binding protein" as used herein refers to antibodies, antibody fragments and other protein constructs which are capable of binding to an antigen.

The terms Fv, Fc, Fd, Fab, or F(ab)2 are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABA™ database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see for example EP-A-0239400 and EP-A-054951.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid $V_{HH}$ dAbs (nanobodies). Camelid $V_{HH}$ are immunoglobulin single variable domain polypeptides that are derived from species including camel, llama, alpaca, dromedary, and guanaco, which produce heavy chain antibodies naturally devoid of light chains. Such Van domains may be humanized according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain.

As used herein, the term "antigen-binding site" refers to a site on a protein which is capable of specifically binding to antigen, this may be a single domain, for example an epitope-binding domain, or it may be paired $V_H/V_L$ domains as can be found on a standard antibody. In some aspects of the invention single-chain Fv (ScFv) domains can provide antigen-binding sites.

The terms "mAbdAb" and "dAbmAb" are used herein to refer to antigen-binding proteins of the present invention. The two terms can be used interchangeably, and are intended to have the same meaning as used herein.

The pharmaceutical formulation of the present invention provides about 150 to 250 mg/mL antigen binding protein; about 1 to 100 mM of a buffering agent providing a pH of about 5.0 to about 7.0; and about 70 to 170 mM of a tonicity agent. Alternatively, the pharmaceutical formulation of the present invention provides about 150 to 250 mg/mL antigen binding protein; about 1 to 100 mM of a buffering agent providing a pH of 6.0±0.5; about 1 to 100 mM of a stabilizer; about 90 to 150 mM of a tonicity agent; and about 0.005 to 0.015% (w/v) of a nonionic surfactant. In one embodiment the antigen binding protein is an anti-B Lymphocyte Stimulator (anti-BLyS) protein antibody.

Also described is a pharmaceutical formulation comprising about 150 to 250 mg/mL antigen binding protein; about 1 to 100 mM histidine at pH of 6.0±0.5; about 70 to 170 mM NaCl. In one embodiment the formulation further comprises about 0.005 to 0.03% (w/v) of a nonionic surfactant. In one embodiment the formulation further comprises about 0.01 to about 0.1 mM of a metal chelator. In one embodiment the antigen binding protein is an anti-IL-13 antibody.

The pharmaceutical formulation of the present invention may be provided in liquid form or may be provided in lyophilized form.

The pharmaceutical formulation according to the present invention comprises a buffering agent. Buffering agents include, but are not limited to citric acid, HEPES, histidine, potassium acetate, potassium citrate, potassium phosphate ($KH_2PO_4$), sodium acetate, sodium bicarbonate, sodium citrate, sodium phosphate ($NAH_2PO_4$). Tris base, and Tris-HCl. In one embodiment, the buffering agent is histidine. In certain embodiments, the histidine concentration is about 5, 10, 15, 20, 25, 30, 35, 40, 45, 50, 55, 60, 65, 70, 75, 80, 85, 90, 95, or 100 mM. In one embodiment the histidine concentration is 10±5 mM. In one embodiment, the histidine concentration is 10-2 mM. In one embodiment, the histidine concentration is about 10 mM. In one embodiment, the histidine concentration is about 15 mM.

As used herein the term "buffering agent providing a pH of about 5.0 to about 7.0" refers to an agent which provides that the solution comprising it resists changes in pH by the action of its acid/base conjugate components. The buffer used in the formulations in accordance with the present invention may have a pH in the range from about 5.5 to about 6.5, or from about 5.8 to about 6.2. In one embodiment the pH is about 6.0. In one embodiment the pH is about 6.250. Examples of buffering agents that will control the pH in this range include acetate, succinate, gluconate, histidine, citrate, glycylglycine and other organic acid buffers. The most suitable buffer in accordance with the present invention is a histidine buffer, such as e.g. L-histidine.

A "histidine buffer" is a buffer comprising the amino acid histidine. Examples of histidine buffers include histidine chloride, histidine acetate, histidine phosphate, histidine sulfate. The histidine formulation identified in the examples as being most suitable is a histidine buffer made from 0.65 mg/mL L-histidine, 1.2 mg/mL L-histidine monohydrochloride.

The pharmaceutical formulation according to the present invention comprises a tonicity agent. Tonicity agents, include, but are not limited to dextrose, glycerin, mannitol, potassium chloride, and sodium chloride. In one embodiment the tonicity agent is sodium chloride. In one embodiment the sodium chloride concentration is about 70 to 170 mM; about 90-150 mM; or about 115±10 mM. In certain embodiments the sodium chloride concentration is about 70, 75, 80, 85, 90, 95, 100, 105, 110, 115, 120, 125, 130, 135, 140, 145, 150, 155, 160, 165, 170, or 175 mM. In one embodiment, the sodium chloride concentration is about 115 mM. In another embodiment, the sodium chloride concentration is 150±10 mM. In one embodiment, the sodium chloride concentration is about 150 mM.

By "isotonic" is meant that the formulation has essentially the same osmotic pressure as human blood. Isotonic formulations will generally have an osmotic pressure from about 250 to 350 mOsm. Isotonicity can be measured using a vapor pressure or freezing-point depression type osmometer.

In certain embodiments the pharmaceutical formulation according to the present invention comprises a stabilizer. Stabilizers, include, but are not limited to human serum albumin (hsa), bovine serum albumin (bsa), α-casein, globulins, α-lactalbumin, LDH, lysozyme, myoglobin, ovalbumin, and RNase A. Stabilizers also include amino acids and their metabolites, such as, glycine, alanine (α-alanine, β-alanine), arginine, betaine, leucine, lysine, glutamic acid, aspartic acid, proline, 4-hydroxyproline, sarcosine, γ-aminobutyric acid (GABA), opines (alanopine, octopine, strombine), and trimethylamine N-oxide (TMAO). In one embodiment the stabilizer is an amino acid. In one embodiment the amino acid is arginine. In one embodiment the arginine concentration is about 20 to 30 mM. In one embodiment the arginine concentration is about 25±2 mM.

In certain embodiments the pharmaceutical formulation according to the present invention comprises a nonionic surfactant. Nonionic surfactants, include, but are not limited to, polyoxyethylensorbitan fatty acid esters (such as polysorbate 20 and polysorbate 80), polyethylene-polypropylene copolymers, polyethylene-polypropylene glycols, polyoxyethylene-stearates, polyoxyethylene alkyl ethers, e.g. polyoxyethylene monolauryl ether, alkylphenylpolyoxyethylene ethers (Triton-X), polyoxyethylene-polyoxypropylene copolymer (Poloxamer, Pluronic), sodium dodecyl sulphate (SDS). In one embodiment the nonionic surfactant is polysorbate 80. In one embodiment the polysorbate 80 concentration is about 0.005 to 0.02% (w/v). In one embodiment, the polysorbate 80 concentration is about 0.01% (w/v). In one embodiment, the polysorbate 80 concentration is about 0.02% (w/v).

In certain embodiments the pharmaceutical formulation according to the present invention comprises a metal chelator. Metal chelators, include, but are not limited to EDTA and EGTA. In one embodiment the metal chelator is EDTA. In one embodiment the EDTA concentration is about 0.01 to about 0.02 mM. In one embodiment, the EDTA concentration is about 0.05 mM.

In one embodiment, the antigen binding protein is a monoclonal antibody or fragment thereof. In one embodiment, the monoclonal antibody or fragment thereof is mouse, chimeric, humanized, or fully human. In one embodiment, the monoclonal antibody or fragment thereof binds to BLyS or IL-13.

In one aspect the formulation comprises the antigen binding protein, histidine, arginine, NaCl, and polysorbate 80. In another aspect the formulation comprises about 200 mg/mL antigen binding protein, about 10 mM histidine, about 25 mM arginine, about 115 mM NaCl, and about 0.01% polysorbate 80, at about pH 6.0. In one embodiment, the antigen binding protein binds to BLyS.

In one embodiment the pharmaceutical formulation of the present invention provides about 200 mg/mL antigen binding protein; about 15 mM histidine at a pH of about 6.25; about 150 mM NaCl; about 0.02% (w/v) polysorbate 80; and about 0.05 mM EDTA. In one embodiment, the antigen binding protein binds to IL-13.

In one aspect the pharmaceutical formulation of the present invention is stable upon freezing and thawing. A "stable" formulation is one in which all the protein therein essentially retain their physical stability and/or chemical stability and/or biological activity upon storage at the intended storage temperature, e.g. 2-8° C. It is desired that the formulation essentially retains its physical and chemical stability, as well as its biological activity upon storage. The storage period is generally selected based on the intended shelf-life of the formulation. Furthermore, the formulation should be stable following freezing (to, e.g., −70° C.) and thawing of the formulation, for example following 1, 2 or 3 cycles of freezing and thawing. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc.

In one embodiment, the pharmaceutical formulation of the present invention is suitable for subcutaneous or intramuscular administration.

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

The query sequence may be 100% identical to the subject sequence, or it may include up to a certain integer number of amino acid alterations as compared to the subject sequence such that the % identity is less than 100%. For example, the query sequence is at least 50, 60, 70, 75, 80, 85, 90, 95, 96, 97, 98, or 99%6 identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids in the query sequence or in one or more contiguous groups within the query sequence.

The % identity may be determined across the entire length of the query sequence, including the CDR(s). Alternatively, the % identity may exclude the CDR(s), for example the CDR(s) is 100% identical to the subject sequence and the % identity variation is in the remaining portion of the query sequence, so that the CDR sequence is fixed/intact.

In one embodiment, the antigen binding protein is a monoclonal antibody or fragment thereof. In one embodiment, the monoclonal antibody or fragment thereof is mouse, chimeric, humanized, or fully human. In one embodiment, the monoclonal antibody or fragment thereof binds to BLyS (SEQ ID NO: 1) or a hetero- or homo-trimeric form of BLyS, for example, the monoclonal antibody or fragment thereof binds to the soluble form of BLyS (SEQ ID NO: 10). In one embodiment, the monoclonal antibody comprises heavy and light chain variable regions comprising amino acid sequences that are 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 2 and 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 3, respectively, or amino acid sequences that are 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 4 and 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 5, respectively. In one embodiment, the monoclonal antibody comprises heavy and light chain variable regions comprising amino acid sequences that are 95% identical to SEQ ID NOs: 2 and 3, respectively, or amino acid sequences that are 95% identical to SEQ ID NOs: 4 and 5, respectively. In one embodiment, the monoclonal antibody comprises heavy and light chain variable regions comprising amino acid sequences that are 90% identical to SEQ ID NOs: 2 and 3, respectively, or amino acid sequences that are 90% identical to SEQ ID NOs: 4 and 5, respectively. In one embodiment, the monoclonal antibody comprises heavy and light chain variable regions comprising amino acid sequences set out in SEQ ID NOs: 2 and 3, respectively, or SEQ ID NOs: 4 and 5, respectively. In one embodiment, the monoclonal antibody comprises heavy and light chains comprising amino acid sequences that are 90% identical to, or is 91% identical to, or is 92% identical to, or is 93% identical to, or is 94% identical to, or is 95% identical to, or is 96% identical to, or is 97% identical to, or is 98% identical to, or is 99%6 identical to SEQ ID NO: 6 and 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 7, respectively, or amino acid sequences that are 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 8 and 90% identical to, or is 91% identical to, or is 92% identical to, or is 93% identical to, or is 94% identical to, or is 95% identical to, or is 96% identical to, or is 97% identical to, or is 98% identical to, or is 99% identical to SEQ ID NO: 9, respectively. In one embodiment, the monoclonal antibody comprises heavy and light chains comprising amino acid sequences that are 95% identical to SEQ ID NOs: 6 and 7, respectively, or amino acid sequences that are 95% identical to SEQ ID NOs: 8 and 9, respectively.

In one embodiment, the monoclonal antibody comprises heavy and light chains comprising amino acid sequences that are 90% identical to SEQ ID NOs: 6 and 7, respectively, or amino acid sequences that are 90% identical to SEQ ID NOs: 8 and 9, respectively. In one embodiment, the monoclonal antibody comprises heavy and light chains comprising amino acid sequences set out in SEQ ID NOs: 6 and 7, respectively, or SEQ ID NOs: 8 and 9, respectively. In one embodiment, the monoclonal antibody comprises CDRs comprising amino acid sequences set out in SEQ ID NOs: 11, 12, 13, 14, 15, and 16. In one embodiment, the anti-BLyS antibody is selected from the group of belimumab, tabalumab, and a mixture thereof. In one embodiment the anti-BLyS antibody comprises the heavy and light chain sequences set out in SEQ ID NOs: 6 and 7, respectively.

In one embodiment, the pharmaceutical formulation according to the present invention comprises a monoclonal antibody concentration of 200±20 mg/mL. In one embodiment the antibody concentration is about 200 mg/mL. In one embodiment the anti-BLyS antibody is co-administered concomitantly or sequentially with a corticosteroid. In one embodiment, the corticosteroid is selected from the group consisting of prednisone, prednisolone, hydrocortisone, methylprednisolone and dexamethasone. In one embodiment, the corticosteroid is prednisone.

In one aspect, the present invention provides for a pharmaceutical formulation according to any preceding claim for the treatment of a disease or disorder amenable to treatment with an anti-BLyS antibody. In one embodiment, the present invention is directed to a method of treating a disease or condition which is amenable to treatment with an anti-BLyS antibody in a subject comprising administering a formulation according to the present invention in a subject in an amount effective to treat the disease or condition. In one embodiment the disease or condition is selected from the group consisting of systemic lupus erythematosus, anti-neutrophil cytoplasmic antibody ("ANCA") vasculitis, lupus nephritis, primary Sjögren's syndrome, chronic immune thrombocytopenia, myasthenia gravis, symptomatic Waldenström's macroglobulinaemia, immune desensitizing of patients awaiting kidney transplant, membranous nephropathy, systemic sclerosis, rheumatoid arthritis, multiple myeloma, multiple sclerosis, and kidney failure. In another embodiment the disease or condition is systemic lupus erythematosus. In another aspect the present invention provides for a formulation for use in the treatment of disease selected from the group consisting of systemic lupus erythematosus, anti-neutrophil cytoplasmic antibody ("ANCA") vasculitis, lupus nephritis, primary Sjögren's syndrome, chronic immune thrombocytopenia, myasthenia gravis, symptomatic Waldenström's macroglobulinaemia, immune desensitizing of patients awaiting kidney transplant, membranous nephropathy, systemic sclerosis, rheumatoid arthritis, multiple myeloma, multiple sclerosis, and kidney failure. In another aspect the present invention provides for a formulation for use in the treatment of systemic lupus erythematosus. In another aspect the present invention provides for the use of a formulation in the preparation of a medicament for the treatment of a disease selected from the group consisting of systemic lupus erythematosus, anti-neutrophil cytoplasmic antibody ("ANCA") vasculitis, lupus nephritis, primary Sjögren's syndrome, chronic immune thrombocytopenia, myasthenia gravis, symptomatic Waldenström's macroglobulinaemia, immune desensitizing of patients awaiting kidney transplant, membranous nephropathy, systemic sclerosis, rheumatoid arthritis, multiple myeloma, multiple sclerosis, and kidney failure. In another aspect the present invention provides for the use of a formulation in the preparation of a medicament for the treatment of systemic lupus erythematosus.

In one aspect, the present invention provides for a kit comprising one or more vials containing the formulation of the present invention and instructions for subcutaneous administration of the formulation to a patient. In one embodiment, the kit further comprises an injection device for subcutaneous administration of the formulation to a patient.

In one embodiment, the present invention is directed to an injection device comprising a stable anti-BLyS antibody formulation described herein. For subcutaneous delivery, the formulation may be administered via a suitable device, such as (but not limited to) a syringe; an injection device (e.g. the INJECT-EASE™ and GENJECT™ device); an infusion pump (such as e.g. Accu-Chek™); an injector pen (such as the GENPEN™; or a needleless device (e.g. MEDDECTOR™ and BIOJECTOR™).

The pharmaceutical formulation in accordance with the invention is essentially free from visible (human eye inspection) particles. The sub-visible particles (as measured by light obscuration) should fulfill the following criteria: maximum number of particles ≥10 μm per vial→6000; maximum number of particles ≥25 μm per vial→600.

The pharmaceutical formulation of the pharmaceutically active anti-BLyS antibody in accordance with the invention can be administered as subcutaneous injection, whereby the administration is repeated several times with time intervals of 1, 2, 3, or 4 weeks. In one embodiment the pharmaceutical formulation of the pharmaceutically active anti-BLyS antibody is administered once every week or once every two weeks. The full volume of the injection fluid is in most cases administered within a time period of 1 to 10 minutes, preferably 2 to 6 minutes, most preferably 3±1 minutes.

For the prevention or treatment of disease, the appropriate dosage of the antibody will depend on the type of disease to be treated, as defined above, the severity and course of the disease, whether the antibody is administered for preventive or therapeutic purposes, on the previous therapy, the patient's clinical history and his response to the antibody, and the discretion of the attending physician. The antibody is suitably administered to the patient at one time or over a series of treatments. Depending on the type and severity of the disease, about 1 μg/kg to 50 mg/kg of bodyweight or more specifically between about 0.1 mg/kg to 20 mg/kg of bodyweight) of the antibody is a candidate initial dosage for administration to the patient, whether, for example, by one or more separate administrations, or by continuous infusion. More specifically the dosage of the antibody will be in the range from about 0.05 mg antibody/kg of bodyweight to about 10 mg antibody/kg of bodyweight.

In another embodiment of the invention, an article of manufacture is provided which contains the pharmaceutical formulation of the present invention and provides instructions for its use. This article of manufacture comprises a container. Suitable containers include, for example, bottles, vials (e.g. multiple or dual chamber vials), syringes (such as multiple or dual chamber syringes) and test tubes. The container may be formed from a variety of materials such as glass or plastic. The container holds the formulation and the label on, or associated with, the container may indicate directions for use. The container holding the formulation may be a multi-use vial, which allows for repeat administrations (e.g. from 2 to 6 administrations) of the reconstituted formulation. The article of manufacture may further include other materials desirable from a commercial and user standpoint, including other buffers, diluents, filters, needles, syringes, and package inserts with instructions for use.

The antibody which is formulated in accordance with the present invention is preferably essentially pure and desirably essentially homogeneous. An "essentially pure" antibody means a composition comprising at least about 90% by weight of the antibody, based on total weight of the composition, preferably at least about 95% by weight. An "essentially homogeneous" antibody means a composition comprising at least about 99% by weight of antibody, based on total weight of the composition.

The invention will be more fully understood by reference to the following Examples. They are merely illustrative and should not be construed as limiting the scope of the invention. Minor variations in procedure, e.g. minor changes in time, temperature, quantity, concentration, scale, etc., are not anticipated to affect the outcome of the experiments. All literature and patent citations are incorporated herein by reference.

The Examples are further illustrated by the appended FIGS. 1-20.

EXAMPLES

Example 1: Belimumab Formulations

Container Closure

Schott type I vials with Daikyo D21-7S Flurotec® stoppers and flip off aluminum seals were used in all studies unless otherwise mentioned. This vial and stopper combination is recommended as the Phase 1 configuration. Long term stability samples that were stored >2-8° C. used Gerresheimer 1.0 mL long, 29 G, thin wall, staked, pre-filled syringes with Stelmi 4800 needle shields and Daikyo W4023 Flurotec® plungers, and were set by vacuum with a nitrogen overlay. Samples <2-8° C. were filled into cryogenic vials.

Product Handling Procedures

Prior to all experiments, belimumab was sterile filtered with a 0.22 μm filter and aseptically filled into the chosen container closures. All stability samples were protected from light during storage.

Excipient Selection

Multi-compendial excipients, mandatory for GMP BDS and FDP manufacturing, were used where possible in the screening studies, and used for all formulations in the long term stability study.

Table 2 provides a list of the formulations tested.

TABLE 2

| | Formulation Description | | |
|---|---|---|---|
| Identifier | Buffer conc (mM) | Stabilizing excipient conc (mM) | pH |
| 1 | 10 mM Histidine | 140 mM NaCl | 6.0 |
| 2 | 10 mM Histidine | 280 mM Sucrose | 6.0 |
| 3 | 10 mM Histidine | 140 mM Sucrose, 70 mM NaCl | 6.0 |
| 4 | 10 mM Histidine | 5.4 mM MgCl$_2$, 130 mM NaCl | 6.0 |
| 5 | 10 mM Histidine | 25 mM Arg, 115 mM NaCl | 6.0 |
| 6 | 10 mM Histidine | 280 mM Sorbitol | 6.0 |
| 7 | 10 mM Histidine | 25 mM Arg, 5.4 mM MgCl$_2$, 105 mM NaCl | 6.0 |
| 8 | 10 mM Succinate | 140 mM NaCl | 6.0 |

Long Term Stability

Concentration-Dependent Aggregation in Formulation 1

As expected, aggregation increased with protein concentration (Table 3, FIG. 1). The aggregation rate approximately doubles between 100 mg/mL and 260 mg/mL, but even at 260 mg/mL would only lead to approximately 1% increase in aggregation over 3 years at 2-8° C. at 200 mg/mL belimumab. Note the starting amount of aggregation observed by SEC-HPLC increases as protein concentration increases, although only by approximately 0.1% (0 month row of Table 3).

TABLE 3

| | Effect of Protein Concentration on % Aggregate | | | | |
|---|---|---|---|---|---|
| Month | 100 mg/mL | 140 mg/mL | 180 mg/mL | 220 mg/mL | 260 mg/mL |
| 0 | 0.47% | 0.50% | 0.54% | 0.58% | 0.60% |
| 1 | 0.47% | 0.51% | 0.52% | 0.58% | 0.62% |
| 2 | 0.54% | 0.61% | 0.64% | 0.75% | 0.78% |
| 4 | 0.53% | 0.59% | 0.63% | 0.72% | 0.77% |
| 6 | 0.58% | 0.63% | 0.70% | 0.76% | 0.84% |
| Rate/Month | 0.018% | 0.021% | 0.027% | 0.030% | 0.040% |

Long Term Formulation Candidate Screen

Based on the following results, the formulation candidates were narrowed to the Formulations 1 and 5 after evaluation of the 3 month data, and then Formulation 5 was chosen as the final formulation after 5¼ months.

Appearance, pH, and Osmolality

Figure 2:
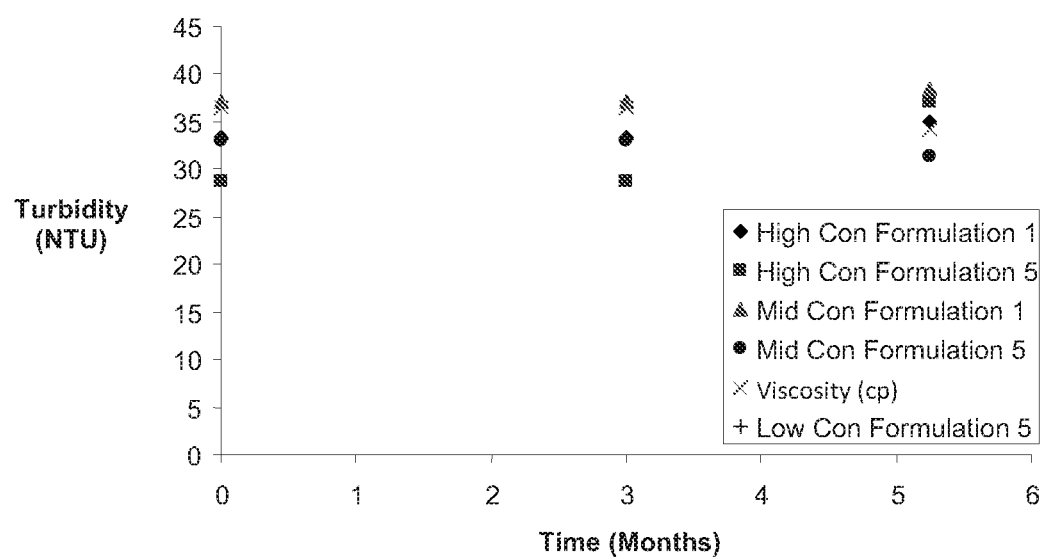
FIG. 2 shows the turbidity of Formulations 1 and 5 after 5' months at 2-8° C.

All samples were opalescent, pale yellow, and free from visible particulate matter at all time points up to 5¼ months. Finished drug product in all eight formulations at all three concentrations most closely matched the Y5 color standard when tested by colorimetry at the initial time point. All FDP samples in the histidine/NaCl (herein referred to as Formulation 1) and the histidine/NaCl/arginine (herein referred to as Formulation 5) formulations also matched the Y5 standard after 3 and 5' months of storage at 2-8° C. Turbidity of the samples with sugar stabilizers (sucrose and sorbitol) was significantly lower than all other samples, which ranged from 29-38 NTU at the initial and 3 month time point. Turbidity also increased in the NaCl containing samples as the protein concentration decreased. Only the Formulations 1 and 5 were tested after 5¼ months at 2-8° C., and showed no response to formulation, concentration or time (FIG. 2).

TABLE 4

| | Turbidity of Long Term Stability Samples after 3 months Storage at 2-8° C. | | | | | |
|---|---|---|---|---|---|---|
| | Turbidity (NTU) | | | | | |
| | High Concentration (~200 mg/mL) | | Mid Concentration (~165 mg/mL) | | Low Concentration (~125 mg/mL) | |
| | 0 Month | 3 Month | 0 Month | 3 Month | 0 Month | 3 Month |
| Hist/NaCl (Formulation 1) | 33 | 33 | 37 | 37 | 37 | 37 |
| Hist/sucrose (2) | 25 | 23 | 24 | 24 | 22 | 23 |
| Hist/sucrose/NaCl (3) | 30 | 30 | 33 | 33 | 34 | 35 |
| Hist/NaCl/MgCl$_2$ (4) | 31 | 31 | 35 | 36 | 36 | 37 |
| Hist/NaCl/Arg (Formulation 5) | 29 | 28 | 33 | 33 | 33 | 34 |
| Hist/Sorbitol (6) | 27 | 27 | 24 | 26 | 26 | 26 |
| Hist/NaCl/Arg/MgCl$_2$ (7) | 29 | 29 | 32 | 31 | 32 | 33 |
| Succinate/NaCl (8) | 31 | 31 | 36 | 35 | 36 | 37 |

The pH of all samples ranged from 6.1 to 6.3 at the initial time point, and did not shift in Formulations 1 and 5 after 5¼ months (Formulation 5 data shown in Table 13). Osmolality was tested only at the initial time point; all samples were 299+/−17 mOsm/kg.

Viscosity and Syringability

Figure 3:
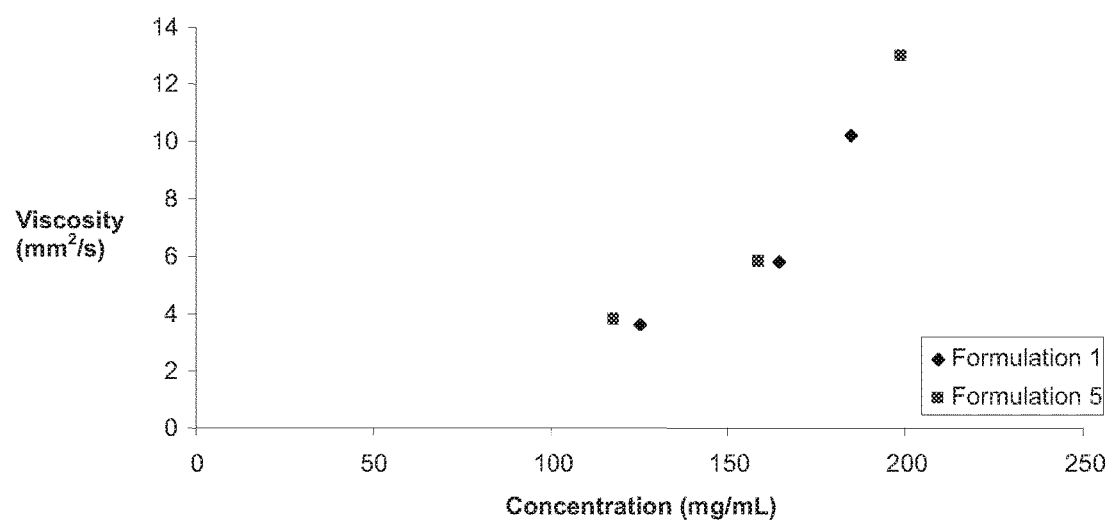
FIG. 3 shows the relationship of belimumab viscosity to concentration.
Figure 4:
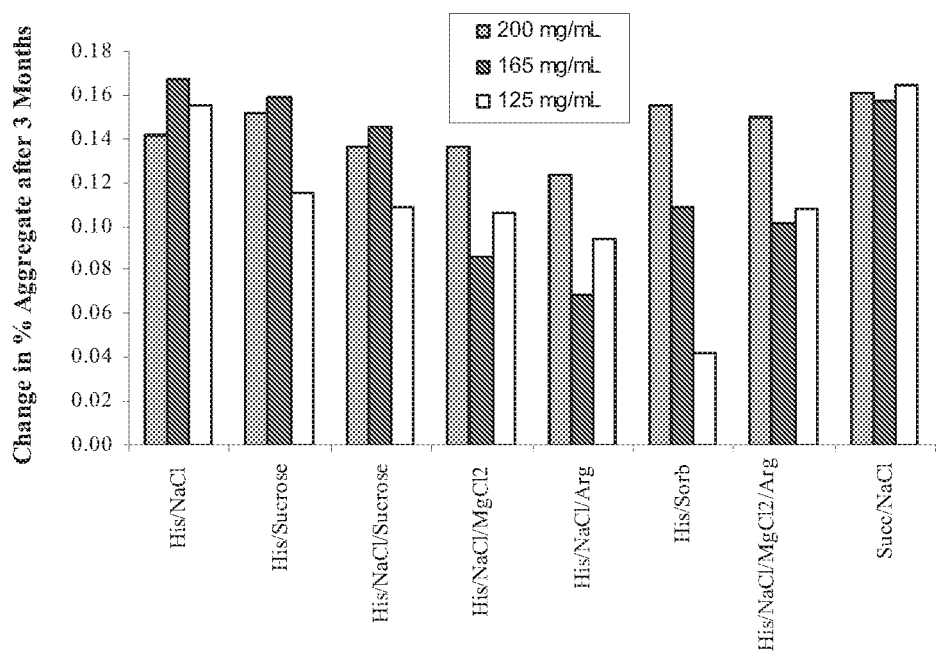
FIG. 4 shows the change in % aggregate after 3 months storage at 2-8° C. for various formulations.

The sugar containing formulations (sucrose, sorbitol) showed the highest viscosities, followed by the succinate/sodium chloride formulation (Table 5). The rest of the salt containing samples were comparable. Viscosity increased exponentially as protein concentration increased in Formulations 1 and 5 (FIG. 3).

TABLE 5

| | Viscosity of Long Term Stability Samples at T0 | | |
|---|---|---|---|
| | Viscosity (mm2/s) | | |
| Sample | High Concentration (~200 mg/mL) | Mid Concentration (~165 mg/mL) | Low Concentration (~125 mg/mL) |
| Hist/NaCl (Formulation 1) | 10.2 | 5.8 | 3.6 |

TABLE 5-continued

Viscosity of Long Term Stability Samples at T0

| Sample | Viscosity (mm2/s) | | |
|---|---|---|---|
| | High Concentration (~200 mg/mL) | Mid Concentration (~165 mg/mL) | Low Concentration (~125 mg/mL) |
| Hist/sucrose | 17.4 | 7.7 | 4.9 |
| Hist/sucrose/NaCl | 13.4 | 7.9 | 3.9 |
| Hist/Nacl/MgCl$_2$ | 12.8 | 5.6 | 3.4 |
| Hist/Nacl/Arg (Formulation 5) | 13.0 | 5.8 | 3.8 |
| Hist/Sorbitol | 21.0 | 7.6 | 4.3 |
| Hist/NaCl/Arg/MgCl$_2$ | 12.8 | 5.6 | 3.5 |
| Succinate/NaCl | 15.3 | 6.6 | 3.8 |

Syringability, measured as force required to deliver 1 mL through the thin walled 29 G needle in 10 seconds, showed similar trends at the initial time point. After 5¼ months, only Formulations 1 and 5 were tested, and there was no significant increase in syringability observed over time at 2-8° C. Syringability over 20 seconds was also tested on one of each syringe at the 5 month time point, and delivery force was shown to decrease by up to 40% when delivery time doubled. While not tested, delivery force can also be decreased by increasing needle gauge.

TABLE 6

Syringability of Long Term Stability Samples at T0 and 5¼ Months

| Sample and Delivery Time | Sample | Syringability (N) | | |
|---|---|---|---|---|
| | | High Concentration (~200 mg/mL) | Mid Concentration (~165 mg/mL) | Low Concentration (~125 mg/mL) |
| Initial Time point 10 Second Delivery | Hist/NaCl (Formulation 1) | 21.9 | 14.5 | 12.0 |
| | Hist/sucrose | 31.3 | 18.2 | 13.8 |
| | Hist/sucrose/NaCl | 25.7 | 17.5 | 12.7 |
| | Hist/NaCl/MgCl$_2$ | 23.8 | 14.1 | 11.1 |
| | Hist/NaCl/Arg (Formulation 5) | 24.4 | 16.3 | 11.5 |
| | Hist/Sorbitol | 35.7 | 18.0 | 12.6 |
| | Hist/NaCl/Arg/MgCl$_2$ | 25.0 | 16.1 | 10.9 |
| | Succinate/NaCl | 28.3 | 14.6 | 11.7 |
| 5¼ month, 2-8° C. Sample 10 Second Delivery | Hist/NaCl (Formulation 1) | 24.4 | 16.1 | 10.6 |
| | Hist/Nacl/Arg (Formulation 5) | 24.2 | 16.7 | 10.8 |
| 5¼ month, 2-8° C. Sample 20 Second Delivery | Hist/NaCl (Formulation 1) | 14.4 | 10.0 | 9.4 |
| | Hist/Nacl/Arg (Formulation 5) | 16.2 | 11.1 | 6.4 |

Forces required to administer drug through seven marketed pen injectors, which are more similar to pre-filled syringes because they require a manual driving force, are similar to the force for belimumab at 200 mg/mL (Table 7). The injection times varied because of different volumes and container diameters, which are listed in Table 7 for comparison. Finally, a University of Nottingham study commissioned by the UK's Department of Trade and Industry has shown that while seated, 59 women between the ages of 16 and 90 were able to apply 53.7 to 237.7N of downward static force at hip level with their thumb. Although neither the pen injector data nor the force study are perfect correlators for using a pre-filled syringe, both data sets build confidence that the viscosity and syringability of 200 mg/mL belimumab are not prohibitive for manual administration. However, the force required to deliver 200 mg/mL belimumab from a 1 mL long pre-filled syringe through a 29 G thin wall needle is at or near the desirable limit for manual injection, and a wider needle would be preferred.

TABLE 7

Injection Forces of Commercially Available Pens at 80 mm/min

| Pen | Provided Needle | Company | Indication | Injection Force (N) | Time to Deliver (seconds) |
|---|---|---|---|---|---|
| Gonal-f RFF | Ypsomed Penfine 29 G x ½" | EMD Serono | Infertility | 22.3 | 5.3 |
| Lantus SoloStar | None (BD recommended) | Sanofi-Aventis | type 2 or Type I diabetes | 6.4* | 11.3 |
| Lantus SoloStar | BD Microfine 30 G x 8 mm | Schering Corporation | chronic hepatitis C | 21.1 | 7.1 |
| Lantus SoloStar | None (BD recommended) | Eli Lilly | diabetes | 24.9* | 7.1 |
| Lantus SoloStar | None (29, 30, 31 G recommended) | Amylin Pharmaceuticals Eli Lilly | type 2 diabetes | 13.4* | 4.1 |
| Lantus SoloStar | None (Novofine recommended) | Novo Nordisk | GH treatment | 13.8* | 9.4 |
| Lantus SoloStar | None (BD recommended) | Eli Lilly | osteoporosis | 24.1* | 5.3 |

*Delivered using a Ypsomed Penfine 29 G x 12.7 mm needle

Size Variants
3 Month SEC-HPLC Data

Aggregation, seen by SEC-HPLC, was the predominate concentration-dependent pathway for belimumab in all formulations. Percent fragmentation (observed as a back shoulder) was variable between 0.1 and 0.2%, but did not change over time (supported by 5¼ month data).

Figure 5:
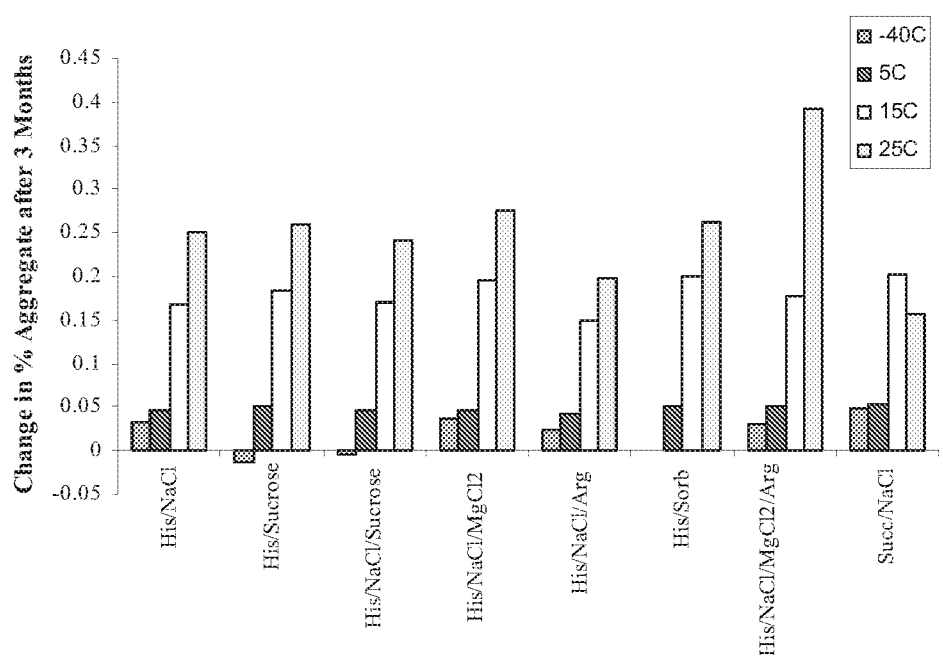
FIG. 5 shows the change in % aggregate after 3 months storage at various temperatures and formulations.

After 3 months at 2-8° C., distinct differences in aggregation rate (FIG. 4) were observed among belimumab formulated in the eight formulations. Formulation 5 (histidine/NaCl/arginine) showed the lowest rate over three months, particularly at 200 mg/mL (blue in FIG. 4). This was supported by the accelerated trends at 200 mg/mL (FIG. 5). Succinate was the worst stabilizer at low temperatures, but the best at elevated temperatures. Many of the other salt and sugar formulations, including Formulation 1 (histidine/NaCl), showed similar absolute aggregate percentages and aggregation rates.

5¼ Month SEC-HPLC Data

Figure 6:
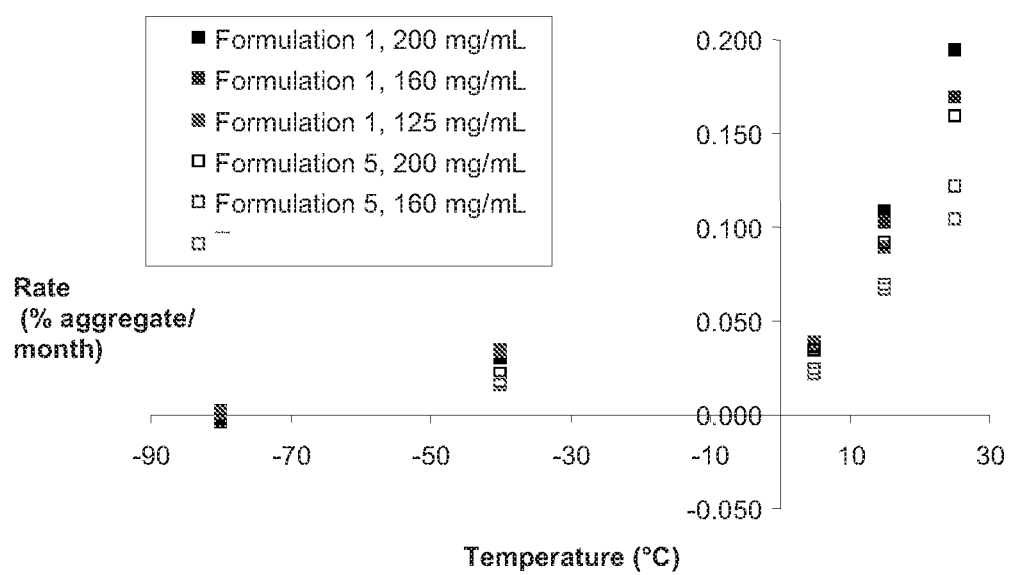
FIG. 6 shows the effect of temperature on aggregation rates after 5 months at up to 25° C., and shows that the arginine formulation (open squares on the graph) significantly dampens aggregation when compared to Formulation 1 (filled squares).
Figure 7:
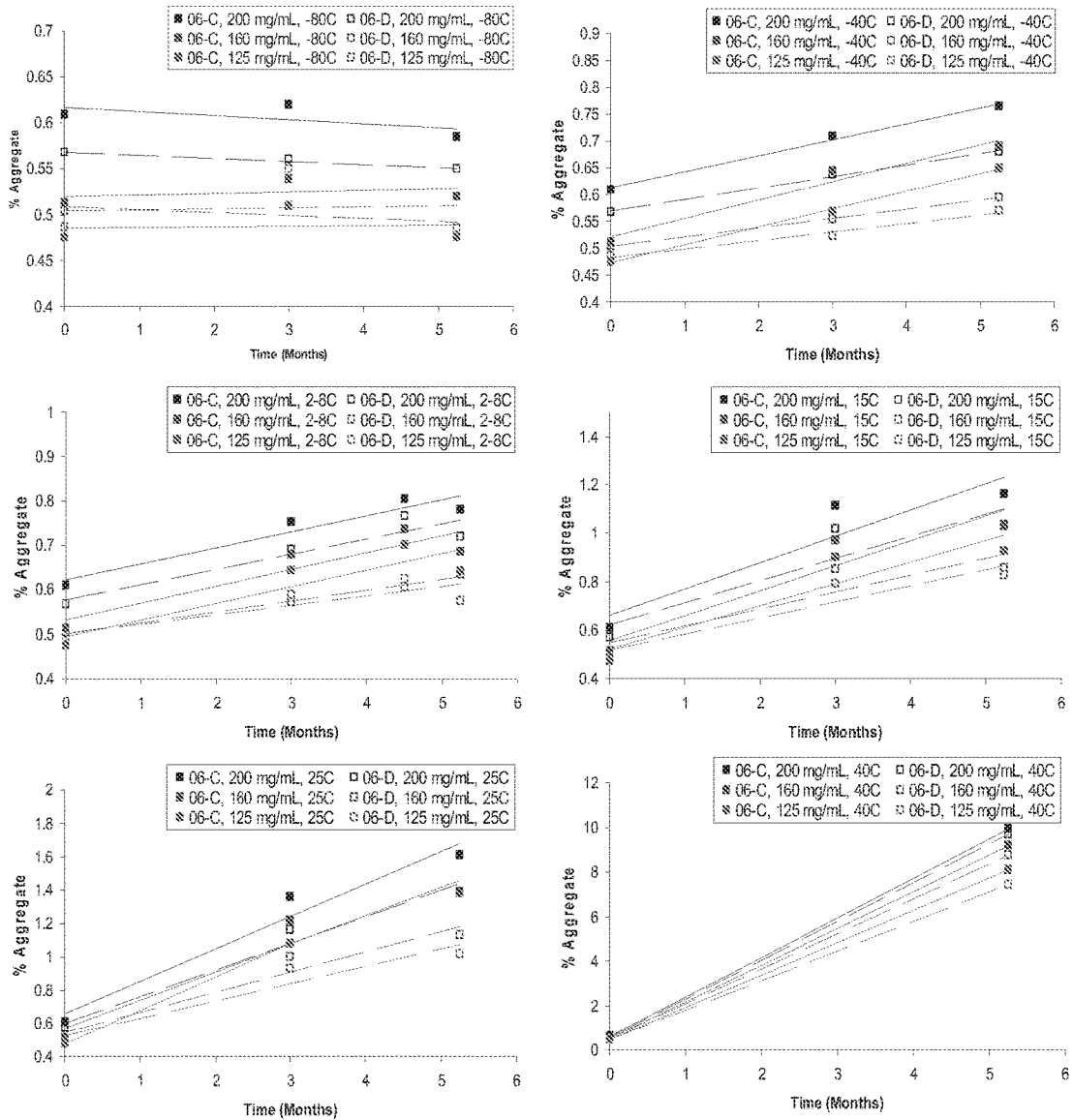
FIG. 7 shows aggregation rates of Formulation 1 (full squares; 06-C) and Formulation 5 (hollow squares; 06-D) between 125 and 200 mg/mL and −80° C. to 40° C. after 5 Months Storage and how consistently Formulation 5 (dashed lines) shows a lower aggregation rate than Formulation 1 (solid lines).

Belimumab in Formulations 1 and 5 were evaluated at 5 months. The trends observed at 3 months continued, with the arginine containing formulation showing a lower aggregation rate, especially at the highest concentration of 200 mg/mL. FIG. 6 shows aggregation rates after 5 months at up to 25° C., and shows that the arginine formulation (open squares on the graph) significantly dampens aggregation when compared to Formulation 1 (filled squares). Further analysis of the aggregation rates at various temperatures in FIG. 7 shows how consistently Formulation 5 (dashed lines) shows a lower aggregation rate than Formulation 1 (solid lines). If the 2-8° C. aggregation rate observed up to 5¼ months holds through 3 years, FDP would only increase by approximately 1.2%.

CGE

Figure 8:
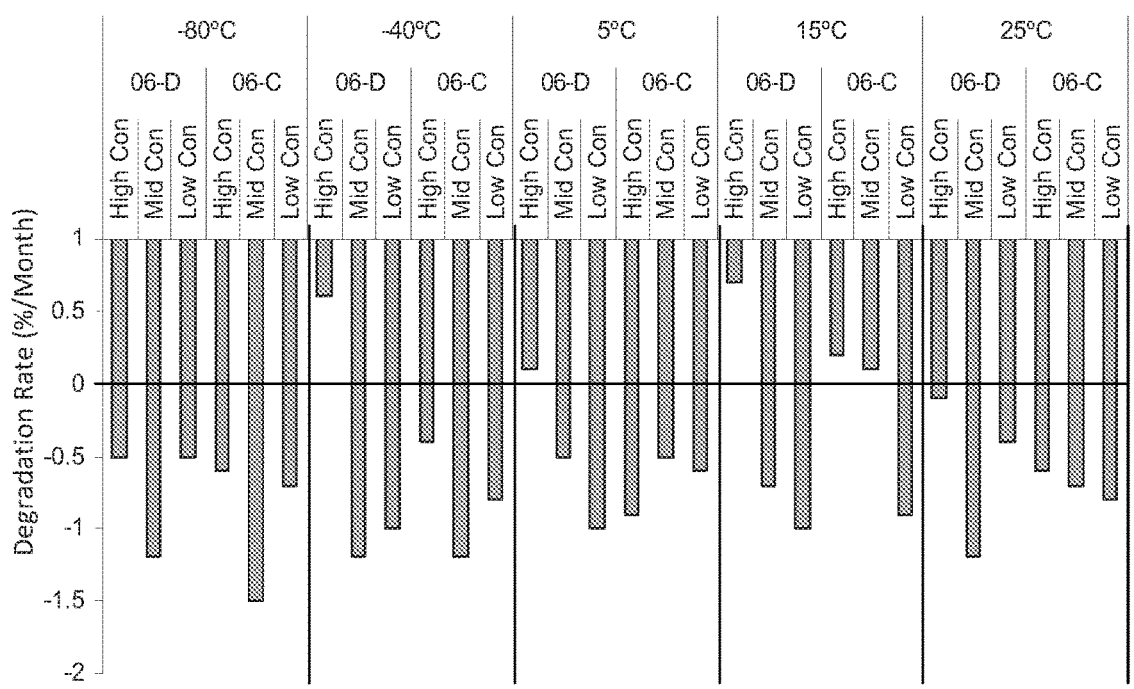
FIG. 8 shows reducing CGE degradation rates of formulations 1 (06-C) and 5 (06-D) between 125 and 200 mg/mL and −80° C. to 40° C. after 5/months storage.

Reducing capillary gel electrophoresis of Formulations 1 and 5 showed no trends after 5 months of storage at various temperatures (rates shown in FIG. 8). Cross-linking and clipping are therefore not dependent on concentration or formulation.

Charge Heterogeneity

Figure 9:
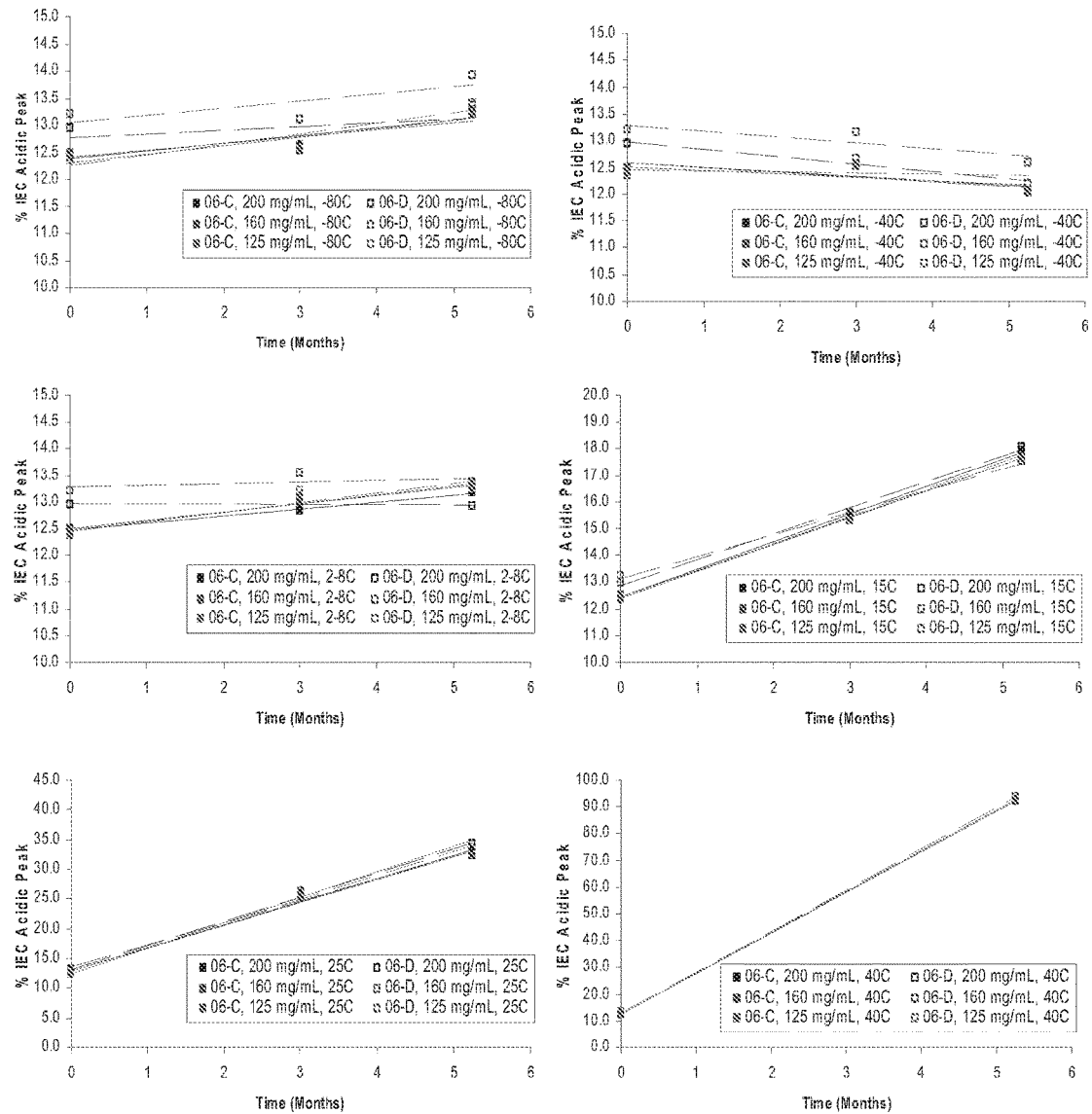
FIG. 9 shows acidic rates of Formulations 1 (full squares: 06-C) and 5 (hollow squares: 06-D) between 125 and 200 mg/mL and −80° C. to 40° C. after 5 months storage.

Ion exchange indicates neither concentration nor the addition of arginine to a histidine buffered salt formulation impacts charge variants (FIG. 9). Although acidic variants increase over time at elevated temperatures, little to no change in variants was observed after 5 months.

Oxidation

Figure 10:
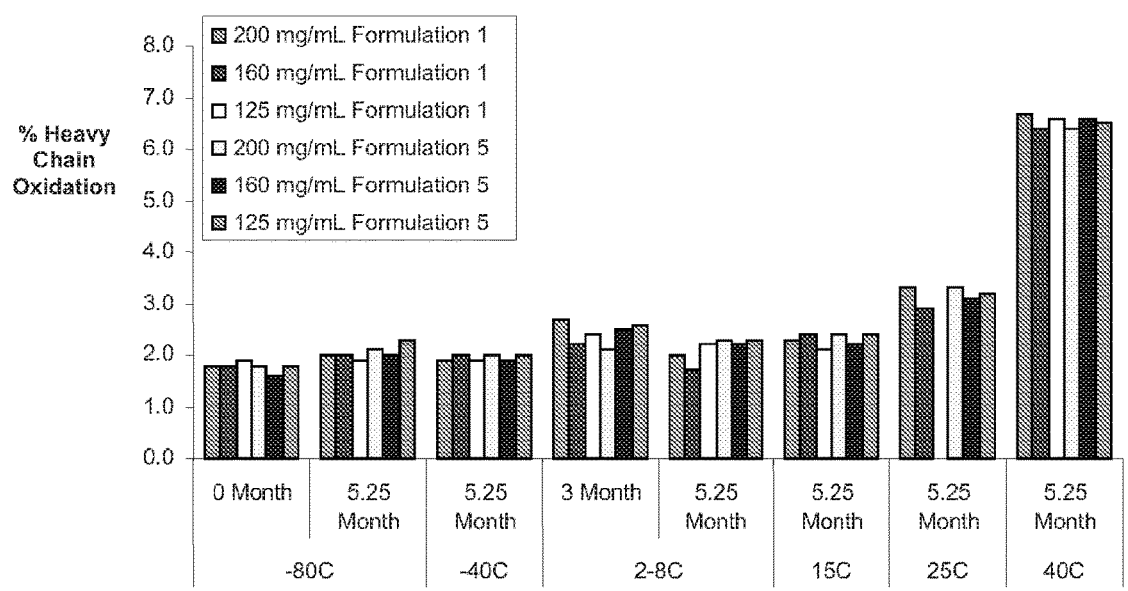
FIG. 10 shows belimumab heavy chain oxidation levels in Formulations 1 and 5 between 125 and 200 mg/mL and −80° C. to 40° C. after 5¼ months storage.

No significant changes in oxidation were observed among any of the 8 formulations after 3 months storage at 2-8° C. (data not shown). After 5 months, when comparing −80° C. and 15° C. data, no differences in oxidation were observed between Formulations 1 and 5 or among the three concentrations in either formulation (FIG. 10). Approximately 1.0% additional oxidation was observed in all samples after 5¼ months storage at 25° C., and approximately 4.5% additional oxidation was observed at 40° C.

Peptide Mapping

Figure 11:
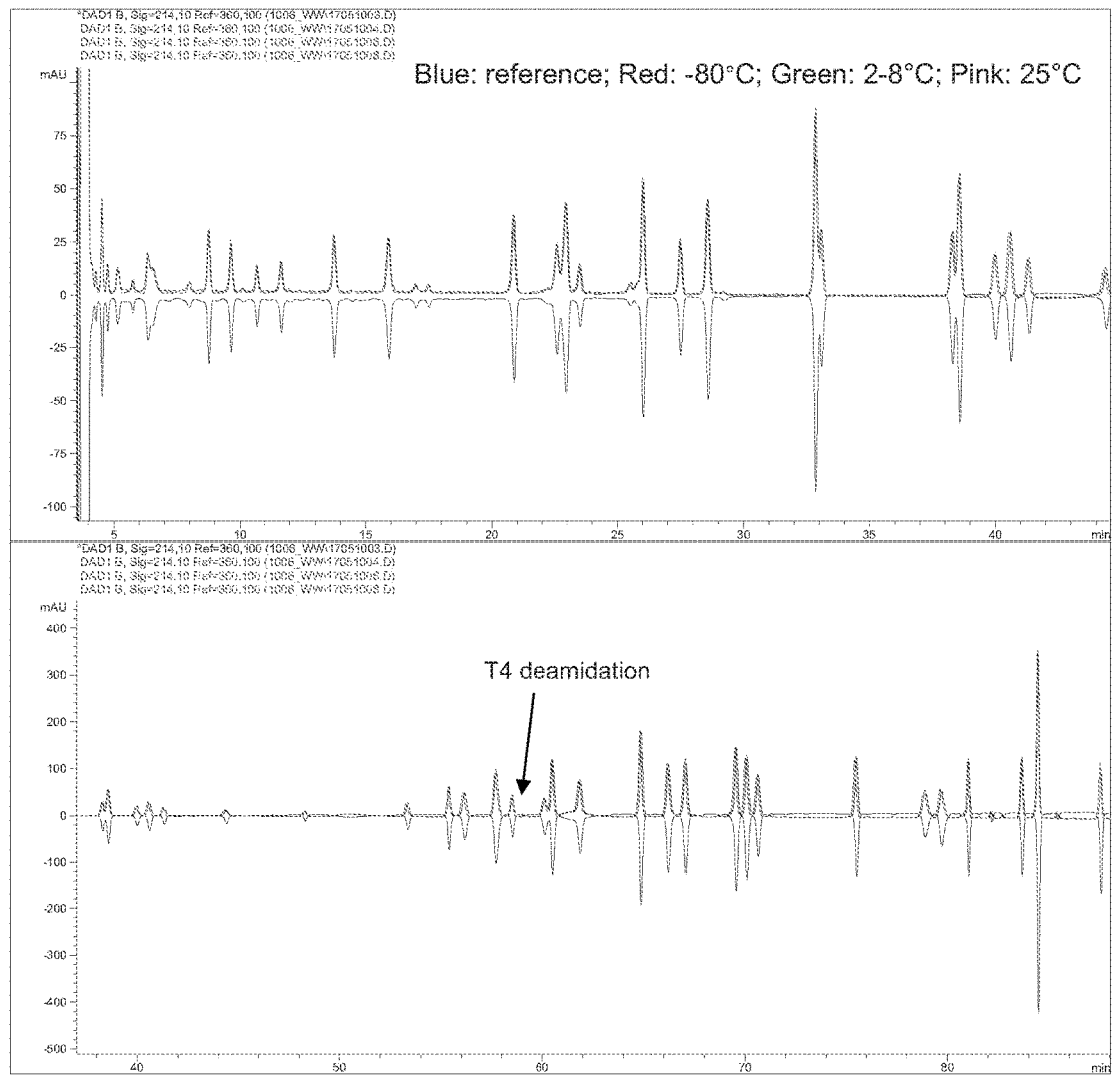
FIG. 11 shows peptide map of belimumab in Formulation 1 at 200 mg/mL after 5¼ months storage.
Figure 12:
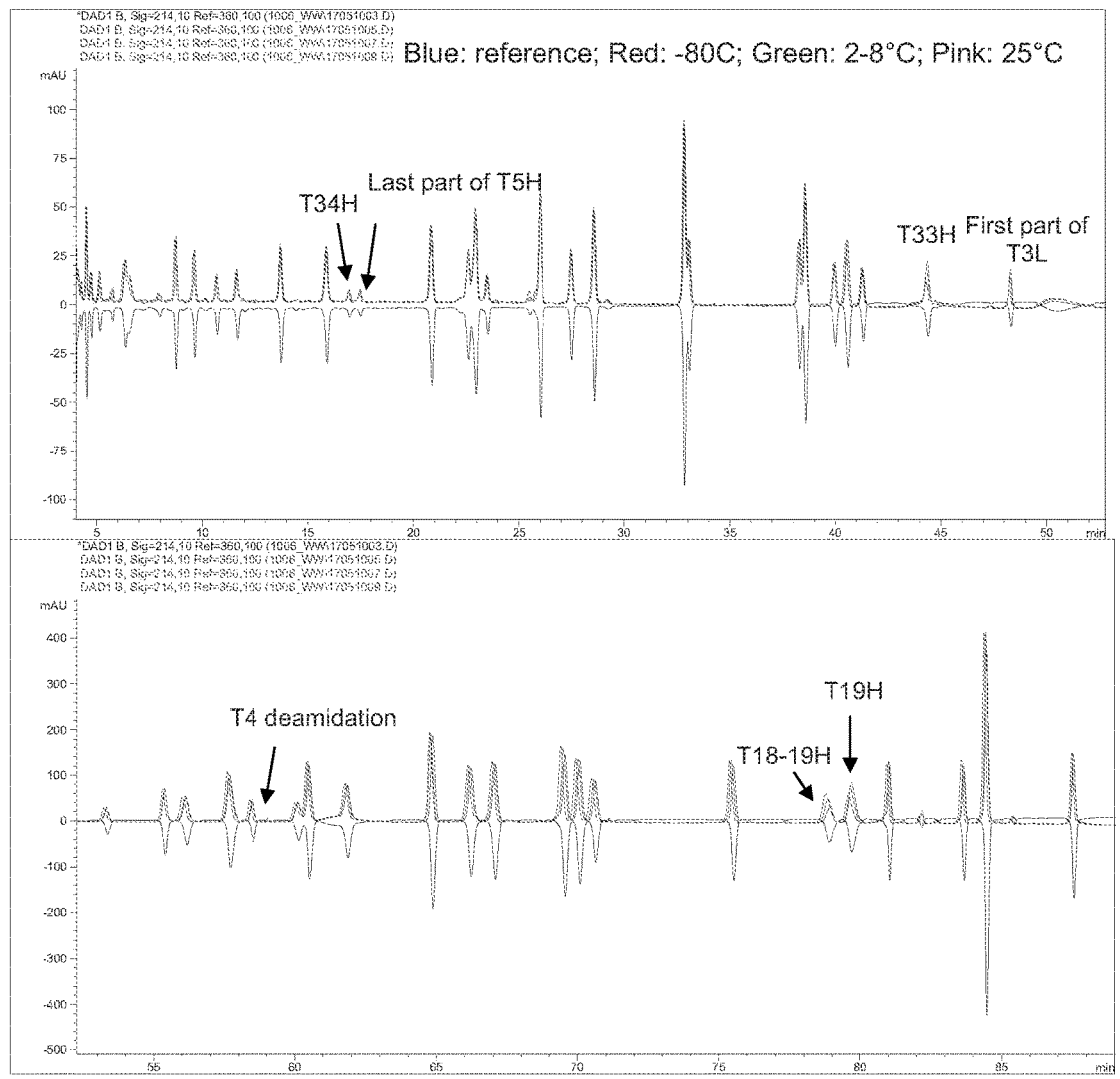
FIG. 12 shows peptide map of belimumab in Formulation 5 at 200 mg/mL after 5¼ months storage.

No differences were observed among the 200 mg/mL Formulation 1 −80° C. and 2-8° C. samples or the reference standard after 5'/% months (FIG. 11). The 25° C. sample showed a small increase in T4 deamidation, as expected at accelerated temperatures. The Formulation 5 sample similarly showed T4 deamidation only at 25° C., but also showed inconsistent peak heights in a number of other peptide peaks (T33, T34 and T5 of the heavy chain, T3 of the light chain in FIG. 12). These peak heights did not trend with temperature, so digestion interference by arginine was suspected.

Figure 13:
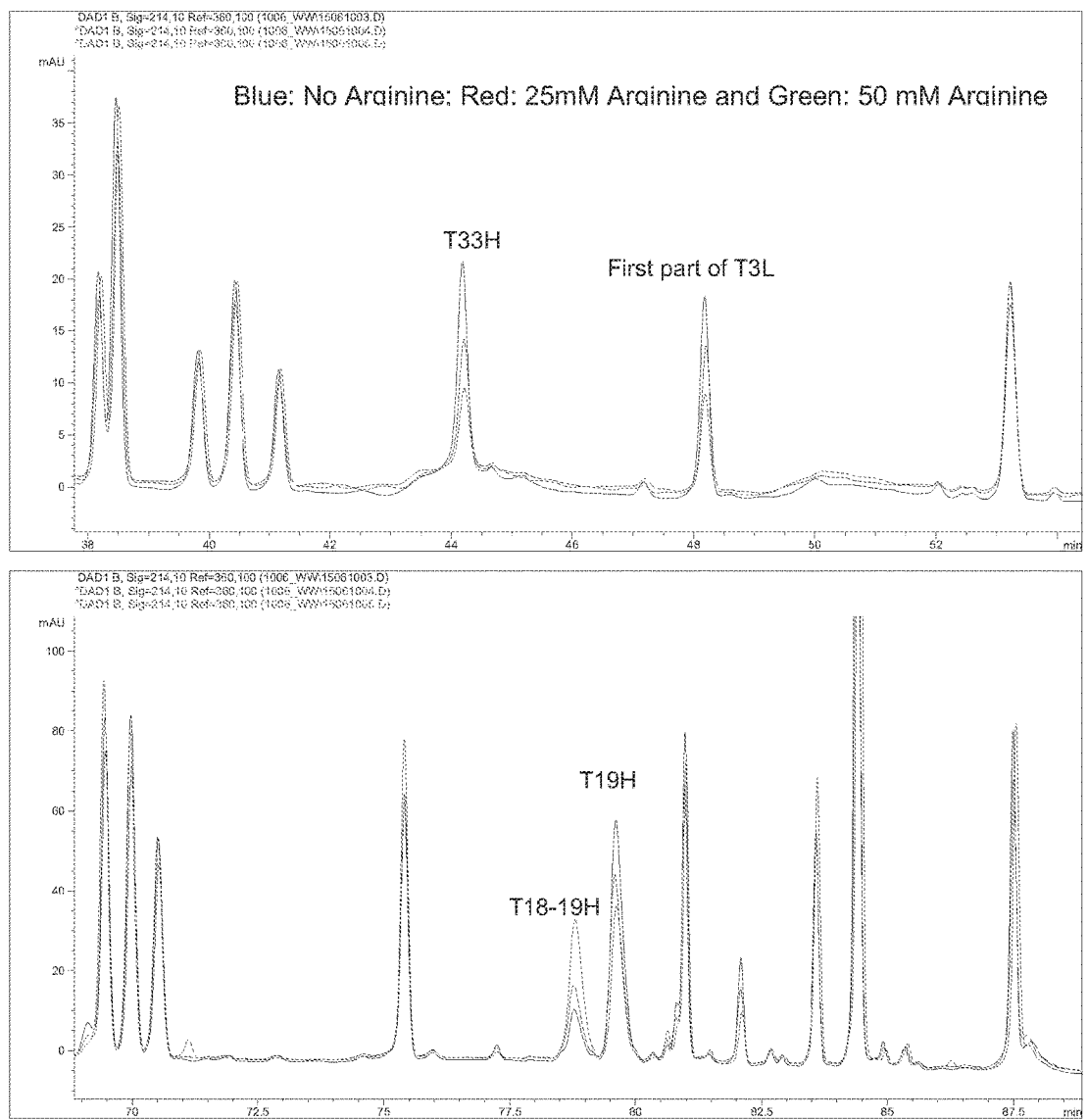
FIG. 13 shows peptide map of belimumab samples with different arginine levels.

To determine if arginine interference was the cause of the variability, 0, 25 and 50 mM arginine were added to a Formulation 1 sample which had been through the method's desalting step. All three samples were then run through the remaining steps, which include trypsin digestion. The same peptide peaks that showed variability in the stability samples showed responses that correlated with arginine concentration (FIG. 13). This indicates the arginine may not always be fully cleared by the desalting step, and explains the temperature independent variation observed in the peptide maps of samples formulated in Formulation 5. Because no other modifications in the peptide maps were observed, it can be surmised that despite the differences in the maps, the Formulations 1 and 5 had no observable degradation after 5¼ months at 2-8° C., and only minimal degradation after 5¼ months at 25° C.

Potency

Belimumab remains biologically active after storage at 2-8° C. for 3 months in either Formulation 1 or Formulation 5 between 125 and 200 mg/mL, or after 5¼ months in Formulation 5 at 200 mg/mL (Table 8).

TABLE 8

Relative Potency after Stability at 2-8° C.

| | % Relative Potency | |
| --- | --- | --- |
| | 3 Months | 5¼ Months |
| 200 mg/mL Formulation 5 | 102% | 118% |
| 125 mg/mL Formulation 5 | 106% | |
| 200 mg/mL Formulation 1 | 90% | |
| 125 mg/mL Formulation 1 | 102% | |

Evaluation of Freeze/Thaw

Samples exposed to 5 fast freeze/thaw cycles between −40° C. and 2-8° C. had a similar amount of aggregation as the −40° C. control samples, indicating fast freeze/thaws are not a concern in either Formulation 1 or the Formulation 5 (Table 9).

TABLE 9

SEC-HPLC Results from belimumab Exposed to Fast Freeze/Thaw

| | % Aggregate | |
| --- | --- | --- |
| | Formulation 1 | Formulation 5 |
| 2-8° C. ctrl | 0.6 | 0.6 |
| −20° C. ctrl | 0.8 | 0.8 |
| −40° C. ctrl | 0.6 | 0.7 |
| −80° C. control | 0.6 | 0.6 |
| −40/2-8° C. 5x Cycle | 0.7 | 0.7 |

Samples exposed to 3 slow freeze/thaw cycles showed a 0.2% increase in aggregate level compared to liquid controls (Table 10).

TABLE 10

SEC-HPLC Results from belimumab Exposed to Slow Freeze/Thaw

| Sample | % Aggregate | % Main Peak | % Clip |
| --- | --- | --- | --- |
| Formulation 1 Liquid Control | 0.7 | 99.1 | 0.2 |
| Formulation 1 Slow freeze/thaw | 0.9 | 98.9 | 0.2 |
| Formulation 5 Liquid Control | 0.6 | 99.2 | 0.1 |
| Formulation 5 Slow freeze/thaw | 0.8 | 99.1 | 0.2 |

DSC

Calorimetry was used to assess the sub-freezing glass transition (Tg') of each formulation and to determine whether a sub-freezing eutectic was formed. Sodium chloride—water eutectic can form below approximately −21° C. and eutectic crystallization of excipients may affect product quality by introducing crystalline surface interactions and changing the local chemical environment in the freeze concentrate containing protein. Storage below Tg' may improve stability by increasing relaxation time and reducing associated degradation.

Formulations 1 and 5 of high concentration belimumab had similar behavior with respect to sub-freezing transitions (Table 11). For Formulation 1, Tg' ranged from −23° C. (fastest freeze) to −33° C. (slowest freeze). For Formulation 5, Tg' ranged from −22° C. (fastest freeze) to −32° C. (slowest freeze). For both formulations, a eutectic endotherm was observed only after thermal cycling with multiple annealing steps at −23° C. The eutectic was most likely sodium chloride—water.

These results indicate that the sub-freezing thermal transitions of these formulations are sensitive to the thermal history of the sample. This is likely due to the high dissolved solids content and the presence of sodium chloride, which can affect Tg' in the protein/amorphous phase. The results, in conjunction with the −80° C. and −40° C. stability data from Section 5.2, also indicate the BDS storage <−40° C. and protected from light is sufficient for belimumab in Formulation 5.

TABLE 11

DSC Results for belimumab in Formulation 5 & Formulation 1

| | Sample | Formulation 1: | Formulation 5: |
|---|---|---|---|
| Fast Freeze | Sample mass (mg) | 16.5 | 16.5 |
| | Tg' | −23° C. | −22° C. |
| | Eutectic endotherm | No eutectic observed | No eutectic observed |
| Medium freeze to −40° C. anneal | Sample mass (mg) | 15.7 | 16.7 |
| | Tg' | −27° C. | −26° C. |
| | Eutectic endotherm | No eutectic observed | No eutectic observed |
| Medium freeze to −23° C. anneal | Sample mass (mg) | 16.9 | 16.3 |
| | Tg' | −25° C. | −27° C. |
| | Eutectic endotherm | No eutectic observed | No eutectic observed |
| Slow freeze to −60° C. | Sample mass (mg) | 17.7 | 16.3 |
| | Tg' | Weak −33° C. | Weak −32° C. |
| | Eutectic endotherm | No eutectic observed | No eutectic observed |
| Thermal cycling (−80/−23° C. with annealing) | Sample mass (mg) | 15.3 | 18.6 |
| | Tg' | After cycling, weak −31° C. | After cycling, weak −28° C. and −18° C. |
| | Eutectic endotherm | Between −16° C. and −12° C. (0.6 J/g) | Between −16° C. and −12° C. (0.7 J/g) |

Evaluation of Shaking

After 48 hours of shaking at 250 rpm, there was no significant change in purity by SEC-HPLC or turbidity in either the vial or the syringe over the range of polysorbate concentrations studied (Table 12). 0.01% polysorbate 80 was shown to be effective and robust in Formulation 5 as a protectant against shaking in both a vial and a syringe.

TABLE 12

SEC-HPLC and Turbidity of belimumab in Formulation 5 after Shaking at 250 rpm

| Container Closure | Sample | % Main Peak by SEC | | | Turbidity (NTU) | |
|---|---|---|---|---|---|---|
| | | 0 hr. | 24 hr. | 48 hr. | 0 hr. | 48 hr. |
| Vial | Control (No Shaking) | 99.4 | 99.3 | 99.3 | 37 | 38 |
| | Low PS80 (0.005%) | 99.4 | 99.3 | 99.3 | 35 | 35 |
| | Target PS80 (0.01%) | 99.4 | 99.3 | 99.3 | 33 | 37 |
| | High PS80 (0.02%) | 99.4 | 99.4 | 99.4 | 30 | 33 |
| Syringe | Control (No Shaking) | 99.4 | 99.3 | 99.3 | 37 | 38 |
| | Low PS80 (0.005%) | 99.4 | 99.3 | 99.3 | 35 | 35 |
| | Target PS80 (0.01%) | 99.4 | 99.3 | 99.3 | 33 | 34 |
| | High PS80 (0.02%) | 99.4 | 99.3 | 99.4 | 30 | 32 |

CONCLUSIONS

A formulation for subcutaneous administration of belimumab at 200 mg/mL was chosen based on its ability to minimize the primary degradation pathway rates (Formulation 5; 0.65 mg/mL L-histidine, 1.2 mg/mL L-histidine monohydrochloride, 6.7-7.3 mg/mL sodium chloride, 5.3 mg/mL L-arginine hydrochloride, 0.1 mg/mL polysorbate 80, pH 6.0; or, alternatively, 10 mM histidine, 115 mM sodium chloride, 25 mM L-arginine hydrochloride, 0.01% (w/v) polysorbate 80, pH 6.0). The aggregation rate (~0.03%/month at 2-8° C.) was shown to increase with belimumab concentration, but was inhibited by the use of 25 mM arginine. The deamidation rate was approximately 0.2%/month at 2-8° C. The 200 mg/mL formulation has an acceptable delivery force for manual or autoinjector delivery using a 1 mL long syringe and a 29 G thin wall or wider needle. Freeze/thaw profiles and storage at −80° C. and −40° C. were shown to be acceptable, and the product is not susceptible to shaking stress.

Long term GMP stability studies were performed on 200 mg/mL belimumab final drug product in Formulation 5 (1.0 mL filled in a 1.0 mL long BD syringe). To date there is 42 months of GMP stability data at intended storage temperature of 2-8° C. (Table 14). The results indicate that Formulation 5 provides adequate stability to belimumab with acceptable degradation profiles observed at the intended storage temperature of 2-8° C. (Table 14).

TABLE 13

Long Term Stability of belimumab in Formulation 5 at 200 mg/mL

| Time (Month) | Temp (° C.) | Appearance | Colorimetry | pH | Turbidity (NTU) | SEC % Aggregate | SEC % Purity | SEC % Fragment | IEC % Acidic | IEC % Main | IEC % Basic Shoulder | IEC Basic (w/o shoulder) | RP % HC Oxidation | CGE % Purity | Potency (% Relative Binding) |
|---|---|---|---|---|---|---|---|---|---|---|---|---|---|---|---|
| 0 | NA | OPF | Y5 | 6.3 | 29 | 0.6 | 99.2 | 0.2 | 12.9 | 78.5 | 5.2 | 8.6 | 1.8 | 95.0 | — |
| 3 | −80 | — | — | 6.2 | — | 0.6 | 99.4 | 0 | 12.6 | 79.4 | 5.0 | 8.0 | 3.8 | 93.1 | 102 |
| | −40 | — | — | 6.2 | — | 0.6 | 99.3 | 0.1 | 12.7 | 79.6 | 4.8 | 7.7 | 3.8 | 93.8 | — |
| | 5 | OPF | Y5 | 6.3 | 29 | 0.7 | 99.1 | 0.2 | 13.0 | 79.3 | 4.9 | 7.7 | 2.2 | 92.4 | 105 |
| | 15 | — | Y5 | 6.3 | — | 1.0 | 98.8 | 0.2 | 15.6 | 76.9 | 4.6 | 7.5 | 4.1 | 95.7 | — |
| | 25 | — | Y5 | 6.1 | — | 1.2 | 98.5 | 0.4 | 25.7 | 68.1 | 3.9 | 6.2 | 4.6 | 93.2 | — |
| 5.25 | −80 | — | — | 6.2 | — | 0.6 | 99.4 | 0.0 | 13.9 | 78.2 | 4.7 | 7.9 | 2.1 | 94.7 | — |
| | −40 | — | — | 6.2 | — | 0.7 | 99.3 | 0.0 | 12.2 | 78.9 | 5.6 | 9.0 | 2.0 | 95.6 | — |
| | 5 | OPF | Y5 | 6.2 | 37 | 0.7 | 99.2 | 0.1 | 12.9 | 78.2 | 5.1 | 8.8 | 2.3 | 94.3 | 118 |
| | 15 | — | — | 6.2 | — | 1.0 | 98.8 | 0.1 | 18.1 | 73.1 | 5.5 | 8.8 | 2.4 | 92.8 | — |
| | 25 | — | — | 6.2 | — | 1.4 | 98.2 | 0.4 | 34.2 | 58.5 | 4.1 | 7.3 | 3.3 | 93.1 | — |
| | 40 | | | 6.2 | — | 9.7 | 88.1 | 2.2 | 92.9 | 2.2 | 3.3 | 4.8 | 6.4 | 83.7 | — |
| 9 | 5 | OPF | Y5 | | — | 0.9 | 99.1 | 0.1 | 14.6 | 78.3 | 4.2 | 7.2 | 2.6 | 96.4 | — |

TABLE 14

GMP Stability Data of 200 mg/mL Belitnumab in Formulation 5 at Intended Storage Temperature of 2-8° C. (1.0 mL in a 1.0 mL Long BD Syringe)

| Test (Analytical Method) | Clinical Acceptance Criteria | Time (Months) | | | | | |
| --- | --- | --- | --- | --- | --- | --- | --- |
| | | 0 | 1 | 2 | 3 | 6 | 9 |
| Appearance [Visual Inspection (Ph. Eur. 2.2.1 and 2.2.2)] | Clear to opalescent, colorless to pale yellow solution, essentially free from foreign particulate matter | OPF | OPF | OPF | OPF | OPF | OPF |
| Charge Heterogeneity (IE-HPLC) | Main Peak (MP): 64.3-89.7% | MP: 75.6 | MP: 75.3 | MP: 74.9 | MP: 74.7 | MP: 75.0 | MP: 74.1 |
| | Acidic Peaks (AP): Report result (X.X %) | AP: 13.2 | AP: 13.4 | AP: 13.6 | AP: 14.1 | AP: 14.1 | AP: 14.9 |
| Container Closure Integrity (Dye leak) | Pass | — | — | — | — | — | — |
| Deliverable Volume (USP <1>, Ph. Eur. 2.9.17) | 1.0-1.1 mL | — | — | — | — | — | — |
| | Maximum volume: X.XX mL | Max: 1.06 | Max: 1.06 | Max: 1.06 | Max: 1.06 | Max: 1.08 | Max: 1.07 |
| | Minimum volume: X.XX mL | Min: 1.04 | Min: 1.05 | Min: 1.05 | Min: 1.05 | Min: 1.05 | Min: 1.05 |
| Injection Forces (Compression Force Test Stand) | Maximum Break Loose Force: Report result (X.X N) | BLF: 7.7 | BLF: 7.0 | BLF: 7.8 | BLF: 7.1 | BLF: 7.5 | BLF: 7.1 |
| | Maximum Peak Extrusion Force: Report result (X.X N) | PEF: 7.4 | PEF: 9.1 | PEF: 8.1 | PEF: 8.6 | PEF: 7.5 | PEF: 7.2 |
| pH [pH Electrode (USP <791>, Ph. Eur. 2.2.3)] | 6.0 +/− 0.4 | 6.0 | 6.0 | 6.0 | 6.0 | 6.0 | 6.0 |
| Potency (Inhibition of Binding) | 75-133% relative potency | 105 | 105 | 96 | 98 | 98 | 99 |
| Protein Concentration (A280) | 200 +/− 40 mg/mL | 200 | 204 | 195 | 202 | 197 | 200 |
| Purity (SDS-PAGE: Reduced with Coomassie Blue Stain) | >=95% | 99 | 98 | 99 | 98 | 99 | 98 |
| Purity (SEC-HPLC) | Main Peak (MP): >=95.0% | MP: 99.4 | MP: 99.4 | MP: 99.2 | MP: 99.2 | MP: 99.2 | MP: 99.1 |
| | Aggregate (AG): Report result (X.X %) | AG: 0.5 | AG: 0.6 | AG: 0.7 | AG: 0.7 | AG: 0.8 | AG: 0.8 |
| | Fragment (FG): Report result (X.X %) | FG: 0.1 | FG: 0.0 | FG: 0.0 | FG: 0.0 | FG: 0.1 | FG: 0.1 |
| Sterility (USP <71>, Ph. Eur. 2.6.1) | No growth | No growth | — | — | — | — | — |
| Subvisible Particulate Matter (USP <788>, Ph. Eur. 2.9.19) | Meets USP <788> and Ph. Eur. 2.9.19 | Meets USP <788> and Ph. Eur. 2.9.19 | — | — | — | — | — |
| | <=6000 particles per container >=10 um | 62 | | | | | |
| | <=600 particles per container >=25 um | 6 | | | | | |

TABLE 14-continued

GMP Stability Data of 200 mg/mL Belitnumab in Formulation 5 at Intended Storage
Temperature of 2-8° C. (1.0 mL in a 1.0 mL Long BD Syringe)

| Test (Analytical Method) | Clinical Acceptance Criteria | Time (Months) | | | | | |
| --- | --- | --- | --- | --- | --- | --- | --- |
| | | 12 | 18 | 24 | 30 | 36 | 42 |
| Appearance [Visual Inspection (Ph. Eur. 2.2.1 and 2.2.2)] | Clear to opalescent, colorless to pale yellow solution, essentially free from foreign particulate matter | OPF | OPF | OPF | OPF | OPF | OPF |
| Charge Heterogeneity (IE-HPLC) | Main Peak (MP): 64.3-89.7% | MP: 72.0 | MP: 72.3 | MP: 70.7 | MP: 69.4 | MP: 69.2 | MP: 68.3 |
| | Acidic Peaks (AP): Report result (X.X %) | AP: 16.3 | AP: 16.2 | AP: 17.7 | AP: 19.3 | AP: 20.1 | AP: 20.8 |
| Container Closure Integrity (Dye leak) | Pass | Pass | — | Pass | Pass | Pass | Pass |
| Deliverable Volume (USP <1>, Ph. Eur. 2.9.17) | 1.0-1.1 mL | — | — | — | — | — | — |
| | Maximum volume: X.XX mL | Max: 1.06 | Max: 1.06 | Max: 1.06 | Max: 1.06 | Max: 1.06 | Max: 1.07 |
| | Minimum volume: X.XX mL | Min: 1.05 | Min: 1.05 | Min: 1.05 | Min: 1.05 | Min: 1.04 | Min: 1.05 |
| Injection Forces (Compression Force Test Stand) | Maximum Break Loose Force: Report result (X.X N) | BLF: 8.0 | BLF: 8.1 | BLF: 7.3 | BLF: 6.8 | BLF: 8.4 | BLF: 9.5 |
| | Maximum Peak Extrusion Force: Report result (X.X N) | PEF: 7.6 | PEF: 9.2 | PEF: 9.3 | PEF: 7.5 | PEF: 9.9 | PEF: 8.4 |
| pH [pH Electrode (USP <791>, Ph. Eur. 2.2.3)] | 6.0 +/- 0.4 | 6.0 | 6.1 | 6.0 | 6.0 | 6.1 | 6.1 |
| Potency (Inhibition of Binding) | 75-133% relative potency | 108 | 93 | 105 | 96 | 98 | 98 |
| Protein Concentration (A280) | 200 +/- 40 mg/mL | 198 | 197 | 199 | 197 | 198 | 197 |
| Purity (SDS-PAGE: Reduced with Coomassie Blue Stain) | >=95% | 99 | 99 | 99 | 99 | 99 | 99 |
| Purity (SEC-HPLC) | Main Peak (MP): >=95.0% | MP: 99.1 | MP: 99.0 | MP: 98.9 | MP: 98.8 | MP: 98.7 | MP: 98.8 |
| | Aggregate (AG): Report result (X.X %) | AG: 0.8 | AG: 0.9 | AG: 1.0 | AG: 1.0 | AG: 1.1 | AG: 1.0 |
| | Fragment (FG): Report result (X.X %) | FG: 0.1 | FG: 0.1 | FG: 0.1 | FG: 0.1 | FG: 0.2 | FG: 0.1 |
| Sterility (USP <71>, Ph. Eur. 2.6.1) | No growth | — | — | — | — | — | — |
| Subvisible Particulate Matter (USP <788>, Ph. Eur. 2.9.19) | Meets USP <788> and Ph. Eur. 2.9.19 | Meets USP <788> and Ph. Eur. 2.9.19 | Meets USP <788> and Ph. Eur. 2.9.19 | — | Meets USP <788> and Ph. Eur. 2.9.19: | Meets USP <788> and Ph. Eur. 2.8.19 | Meets USP <788> and Ph. Eur. 2.9.19 | Meets USP <788> and Ph. Eur. 2.9.19 |
| | <=6000 particles per container >=10 um | 45 | | 290 | 176 | 179 | 293 |
| | <=600 particles per container >=25 um | 0 | | 12 | 16 | 7 | 10 |

Appearance key: C = Clear, O = Opalescent; L = Colorless, P = Pale yellow, Y = Yellow; F = essentially free from foreign particulate matter; X = other
Injection Force: BLF = Break Loose Force, PEF = Peak Extrusion Force,

Example 2: Anti-IL13 is a High Concentration-High Dose mAb

Anti-IL13 is a glycosylated humanized mAb (IgG1) directed against human interleukin-13 (IL13). In order to achieve a very high clinical dose (10 mg/kg) for subcutaneous delivery, based on PK/PD modelling, the drug substance and drug product needed to be developed at a concentration of 200 mg/mL in a vial presentation. As a direct consequence of achieving a much higher concentration of mAb in the vial, various formulation challenges for anti-IL13 were presented such as: (i) to identify a unique formulation able to support the stability, manufacturability, analytical and delivery challenges of a high concentration monoclonal antibody intended for delivery at a high clinical dose via subcutaneous delivery, (ii) to prevent analytical and stability challenges arising due to gelation of the monoclonal antibody at higher concentrations (iii) to prevent various related challenges that may arise especially during delivery of the monoclonal antibody in an injection volume of 1.5 mL or less. As a direct finding revealed during the formulation development work, it was determined that this monoclonal antibody had a tendency to form irreversible gel like matrix in certain buffer systems at elevated temperatures, therefore, posing significant risk of instability of the protein. Viscosity increases exponentially with concentration and may complicate the filtration process. Higher concentration monoclonal antibodies have greater susceptibility to aggregation with increased risks of particulates formation and reversible self association. Therefore, high-throughput formulation (HTF) development studies were performed to identify the optimal buffer and pH for the new formulation to support high concentration monoclonal antibody designed to provide a high clinical dose. These along with other bench top studies identified an optimal formulation which prevented the gelation phenomenon at elevated temperatures. The additional formulation development studies were identified various excipients to be included to selected buffer system. These were shake, freeze-thaw, and elevated temperatures studies to assess the physical stability followed by short and long-term stability studies to assess the chemical stability of the anti-IL13 mAb. Various other studies were also conducted to ensure that the clinical delivery considerations are met.

Example 3: HTF pH-Buffer Screening: (Identification of Target pH and Buffer)

Previously tested acetate based formulation for anti-IL13 monoclonal antibody at 50 mg/mL had already established that the pH was not optimal. Suboptimal formulation buffer pH could increase instability of a higher concentration anti-IL13 monoclonal antibody solution by altering the charge on the protein and affecting electrostatic interactions. The high concentration formulation development commenced with the identification of an optimum pH as well as determination of the best buffer species.

The study was performed at a mAb concentration of 13 mg/mL. The buffer screening was conducted by means of a HTF process in 96 well plates. The study consisted of a vast range of buffer types and pH levels. Each plate consisted of 48 samples with 2 replicates in random order. Samples were stressed for 3 days at 50° C./ambient RH. The testing included general appearance (GA), concentration at A280 and A260 nm, pH, size exclusion chromatography (SEC), capillary iso-electric focusing (cIEF) and dynamic light scattering (DLS). The tested factors are presented in Table 15.

TABLE 15

| HTF Buffer Screen Study | |
|---|---|
| Factor 1<br>Buffer Type<br>(3 levels) 10, 55, and 100 mM | Factor 2<br>pH<br>(6 levels) |
| Acetate | 4 |
| Acetate, Citrate | 5 |
| Acetate, Citrate, Succinate | 5.5 |
| Acetate, Citrate, Histidine, Succinate | 6 |
| Acetate, Citrate, Histidine, Succinate | 6.5 |
| Histidine, Phosphate | 7 |

The result of the general appearance testing of the plates revealed high levels of precipitation in some of the samples especially in Acetate, Citrate and Phosphate buffer. Succinate buffer was the only buffer species which did not indicate precipitation.

Figure 14:
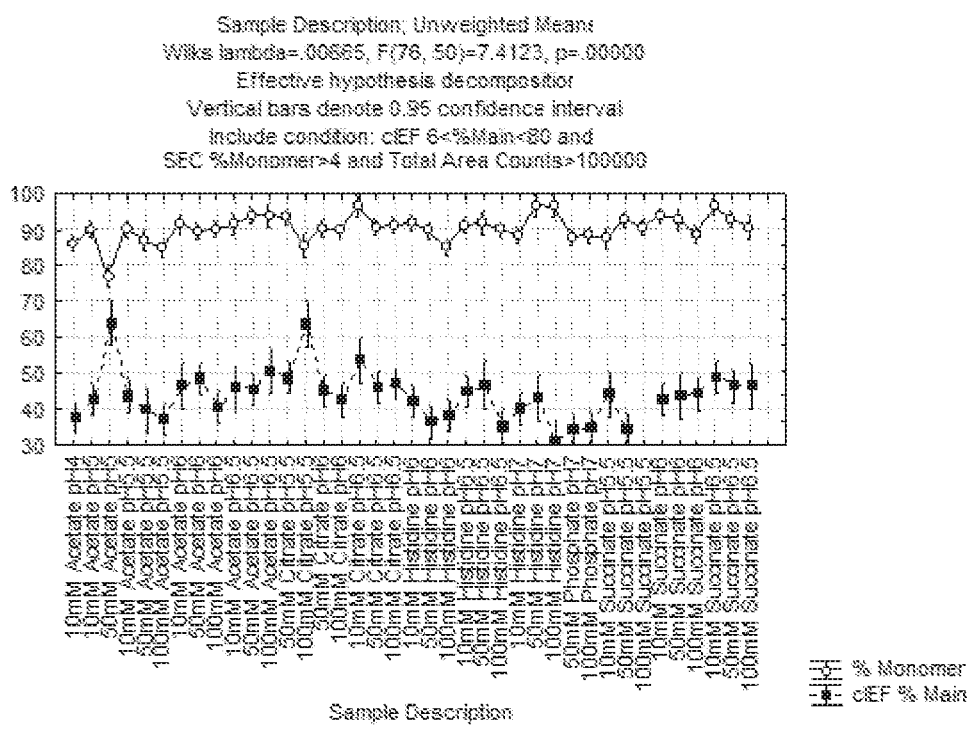
FIG. 14 shows HTF pH-buffer screening.

Deamidation and aggregation profiles were generated for all the samples via cIEF and SEC, respectively. FIG. 14 shows a plot with the overlay of cIEF and SEC data. The plot displayed that the formulations with the highest % Monomer by SEC also had lowered % Main by cIEF indicating that anti-IL13 aggregates at lower pH and deamidates at higher pH1. It can be observed that % Monomer is higher where the pH is 6-7 than at pH 4-5.5 regardless of buffer species.

Overall, the HTF pH-buffer screening led to the following conclusions: (i) Citrate and acetate buffer resulted in the highest numbers of cloudy wells (indication of precipitation) as determined by GA and (ii) Phosphate buffer promoted precipitation along with increase in aggregation and deamidation based on cIEF and SEC results and (iii) anti-IL13 aggregates at lower pH and deamidates at higher pH.

Example 4: HTF pH-Buffer Screening: (Determination of Optimal pH)

A second HTF study was performed based on 3×3 factorial (3 buffers, 3 pHs) DOE design consisting of a total of 90 samples. The selected buffers for the evaluation included acetate, histidine and succinate at the final pH ranges between 5.5 and 6.5. The buffers were selected to be a fixed concentration of 25 mM. The design enabled 6 replicates for each formulation along with 6 replicates of acetate formulation on the stress plate to serve as a control for comparison purposes.

Each plate was stressed for 3 days at 50° C./ambient RH. The testing included general appearance (GA), concentration at A280 and A260 nm, pH1. SEC, cIEF, DLS and DSC (Differential Scanning Calorimetry) on selected samples.

The results of the study were analyzed by statistical software known as Design Expert. Interesting trends were revealed when all the assay results were subjected to a Analysis of variance (ANOVA) test using the same software. Buffer species and pH were found to be significant factors for results by concentration, corrected concentration, DLS, SEC and cIEF.

Figure 15:
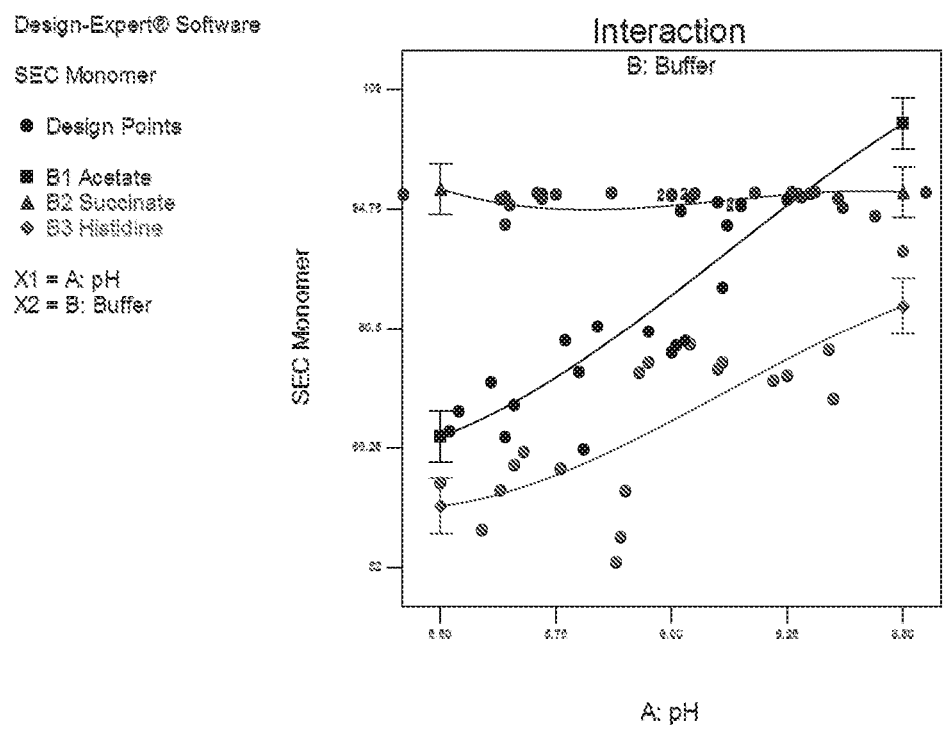
FIG. 15 shows two factor interaction—pH×buffer—SEC monomer.
Figure 16:
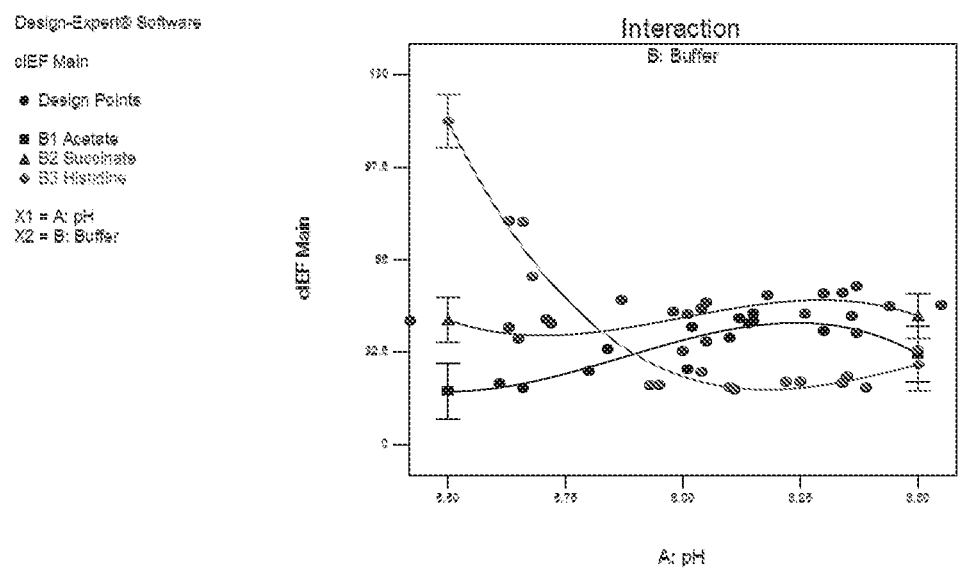
FIG. 16 shows two factor interaction—pH×buffer—cIEF main.

FIG. 15 shows the interaction between pH and buffer species on SEC % monomer. For both acetate and histidine buffers, % monomer increased as pH increased. FIG. 16 shows the interaction of pH11 and buffer on % Main for cIEF. Both pH and buffer were found to be significant. From this plot pH in the range 5.5-6.5 does not appear to affect % Main for either acetate or succinate, but it does for histidine.

Overall, the HTF pH-buffer screening led to the selection of final optimal pH of 6.25.

Example 5: Determination of an Optimal Thermal Stress Condition Based on Thermal Stability Profile by DSC Among various factors that may potentially influence gelation of protein such as concentration, pH, salt content, there is one critical factor that governs this phenomenon-temperature. The thermal stability condition selected for anti-IL13 tested by HTF and other development studies was evaluated by DSC. In general, medium sized globular proteins begin to unfold around 25° C. and for monoclonal antibodies it is around 60° C. The start of unfolding for this mAb under all tested buffers (acetate, histidine and succinate) is around 61° C., indicating a thermally-stable molecule, and confirming that a 50° C. accelerated storage temperature would allow for a folded anti-IL13 monoclonal antibody. Since there is a difference of more than 10° C. between the start of unfolding and the 50° C. accelerated storage condition, it was determined to utilize 50° C. as the storage temperature for screening.

Table 16 lists the Tm values as determined from the raw scans. The Tm1 values span the 71.3-71.6 C range and the Tm2 values span a larger, 83.5-84.1 C, range. There are no significant changes in the Tms of same buffer at different pH values. The variations in Tm1 and Tm2 as measured for all conditions are below 1° C., thus the tested protein solutions have similar thermodynamic stabilities.

TABLE 16

Tm values as determined from the raw scans

| Buffer | Tm1, C. | Tm2, C. |
| --- | --- | --- |
| acetate 6.0 | 71.3 | 84.1 |
| acetate 6.5 | 71.4 | 83.9 |
| histidine 6.0 | 69.9 | 83.6 |
| histidine 6.5 | 71.3 | 84.1 |
| succinate 6.0 | 71.4 | 83.6 |
| succinate 6.5 | 71.6 | 83.5 |

Example 6: Assessment of Feasibility of High Concentration Formulation

The clinical need for subcutaneous (SC) administration of high dose protein-based drugs >100 mg/mL oftentimes introduces additional technical development challenges for manufacturing, analytical testing, stability, and delivery. A common attribute of a high concentration protein formulation is high viscosity, which results directly from the reversible self-association of proteins. A high viscosity may also introduce additional clinical development challenges due to high injection forces, increase in pain at the injection site, and may also alter drug pharmacokinetic profiles. Thus, an important element of product development efforts seek to identify a formulation with a low viscosity. The effect to viscosity may be mitigated by changes in pH or addition of excipients.

Due to the expected exponential increase in viscosity as a result of increase in mAb concentration up to 200 mg/mL, an initial feasibility study was conducted to investigate the viscosity and injectability of a high concentration anti-IL13 solution. A ~150 mg/mL solution was concentrated to ~210 mg/mL in the previously established acetate based formulation. Viscosity measurements were taken at the following mAb concentrations: 50, 150 and 200 mg/mL using a cone and plate rheometer.

Figure 17:
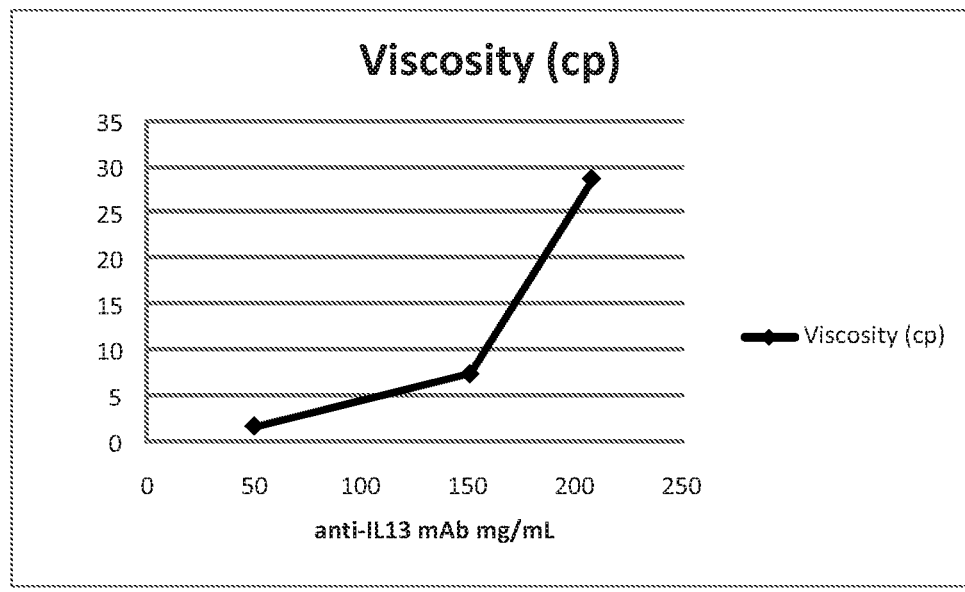
FIG. 17 shows viscosity of anti-IL13 antibody at various concentrations.

FIG. 17 displays the various viscosity levels plotted against the aforementioned concentrations, with an observed exponential increase in viscosity with increasing concentration. The viscosity result for the concentrated solution at 207.7 mg/mL was 28.6 cP.

The maximum injection force was determined by placing 207.7 mg/mL anti-IL13 in a 1 mL glass syringe fitted with a 27 gauge needle with syringe speed set at 3 mm/min measured using Instron electro mechanical testing system. Table 17 shows the numeric results obtained for both viscosity and syringeability at the maximum concentration of 207.7 mg/mL.

The determination of the viscosity (28.6 centipoise) and maximum injection force of 30.3 Newtons at the concentration of 207.7 mg/mL prompted that additional formulation development efforts were required to enable and achieve the feasibility of manufacturing and dosing a high concentration anti-IL13 presentation.

TABLE 17

Summary of High Concentration Feasibility Determination

| | |
| --- | --- |
| Concentration | 207.7 mg/mL |
| Viscosity | 28.6 centipoise |
| Maximum Injection Force | 30.3 Newtons |

Example 7: Assessment of Physical Properties Via Shake Studies

Histidine and succinate buffer at pH 6.25 were identified as the optimal buffer systems, however additional formulation development studies were required to identify suitable formulation for high concentration mAb solutions susceptible to high viscosity dependent on high concentration and gelation as a function of temperature.

The formulations used in the shake studies stemmed from the HTF screening study. The HTF study identified two buffer systems (histidine and succinate at pH 6.25) that provided good stability. A third buffer system (50 mM acetate pH 5.5) was also included as a control. The histidine and succinate pH 6.25 buffer system samples were prepared using small scale buffer exchange and concentration techniques. The following excipients were then added: 0.02% polysorbate 80 (PS80) to protect the protein from shear stress, and 150 mM sodium chloride as a potential viscosity lowering agent.

The samples were filled at 1.2 mL volume in 3 mL glass vial at a 1 mL fill volume and were shaken for 72 hours at 250 rpm at 2-8° C. on a horizontal shaker protected from light. The samples were then tested by various analytical techniques. Table 18 below lists the formulations used for the shear stress/shake study. Lower concentration formulations were included as no previous shake study with 50 mg/mL had been attempted. Control formulations with no excipients such as PS80 were also included. For the acetate samples, NaCl controls were included.

TABLE 18

Shake study design and samples.

| Formulation # | Sample type | mAb conc. (mg/mL) | Buffer system | pH | Surfactant (0.02%) | Viscosity modifier (150 mM) |
|---|---|---|---|---|---|---|
| 1 | Low mAb | 50 | 50 mM Sodium Acetate | 5.5 | PS80 | NaCl |
| 2 | | 50 | 20 mM Sodium Succinate | 6.25 | PS80 | NaCl |
| 3 | | 50 | 20 mM Histidine | 6.25 | PS80 | NaCl |
| 4 | High mAb | 200 | 50 mM Sodium Acetate | 5.5 | PS80 | NaCl |
| 5 | | 200 | 20 mM Sodium Succinate | 6.25 | PS80 | NaCl |
| 6 | | 200 | 20 mM Histidine | 6.25 | PS80 | NaCl |
| 7 | Buffer Controls | 0 | 50 mM Sodium Acetate | 5.5 | | |
| 8 | | 0 | 20 mM Sodium Succinate | 6.25 | | |
| 9 | | 0 | 20 mM Histidine | 6.25 | | |
| 10 | NaCl Control | 200 | 50 mM Acetate | 5.5 | | NaCl |

No significant changes were observed in the general appearance, SEC, DLS and MFI in all samples formulated with NaCl and polysorbate 80. High concentration protein formulations were not stable in the Acetate (Control) formulation via SEC-HPLC results.

Figure 18:
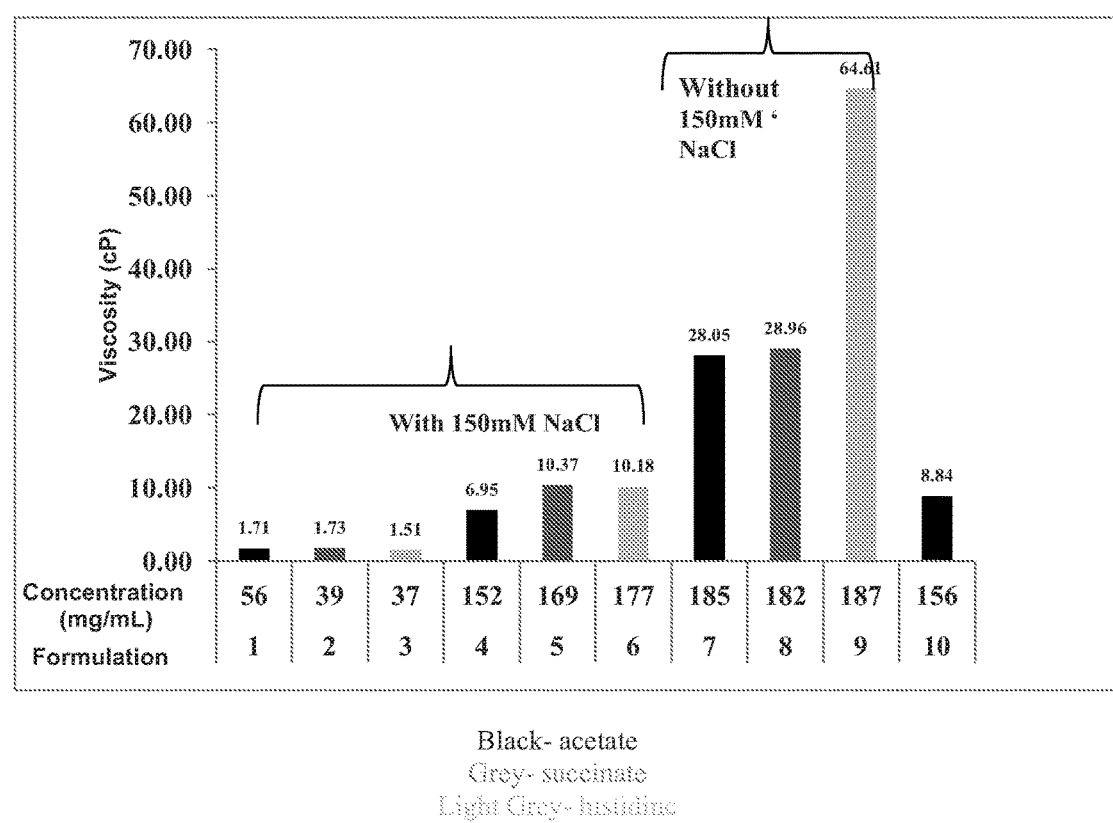
FIG. 18 shows viscosity (cP) vs. concentration (mg/mL) results for anti-IL13 T=1 samples from shake study.

The target concentration of all tested anti-IL13 mAb is 200 mg/mL, however, due to limitations of process yields and inherent variability of the viscosity measurements, the nominal concentration formulations in histidine and succinate at 200 mg/mL is within 10% range. Measurement of the viscosity of samples used in the shake study reveal that a 6 fold lower viscosity is achievable in formulations containing 150 mM Sodium Chloride at a nominal concentration of 200 mg/mL, regardless of the buffer system (FIG. 18). Formulations containing the buffers alone displayed significantly higher viscosity in Histidine compared to Sodium Acetate and Sodium Succinate. This suggested that the sodium ions of the latter buffers may be contributing toward the reduction of the viscosity, thus also explaining that the sodium ions of Sodium Chloride may be responsible for the viscosity lowering effect. However, as Histidine is combined with 150 mM Sodium Chloride, the viscosity is lowered to the same degree as in other buffer systems. This may also suggest that the there is a synergistic effect between the histidine buffer and NaCl which is effectively lowering the viscosity.

This study also included formulations 1, 2, and 3 at a lower concentration of 50 mg/mL; however, no difference was observed among the formulations, indicating the importance of generated stability data for high concentration formulation at the target concentration (data not shown).

The dependence of viscosity on protein concentration and sodium content of the samples is summarized in FIG. 18. The viscosity readings for 50 mg/mL (lower concentration) samples were all less than 2 cps. The viscosity of acetate sample with a nominal concentration of 200 mg/mL containing 150 mM NaCl was about 3 cps lower than the corresponding histidine and succinate samples, primarily due to the lower than nominal concentration of 200 mg/mL due to poor process yields. The overall concentrations were less than 200 mg/mL, due to losses during the concentrated sample preparation as shown in FIG. 18.

The results of the study clearly indicated that inclusion of 150 mM NaCl substantially reduced viscosity across the tested buffer systems. Also a unique insight into the synergistic relationship between the histidine buffer and NaCl was observed.

Note: The target concentration of all tested anti-IL13 mAb is 200 mg/mL, however, due to limitations of process yields and inherent variability of the viscosity measurements, the nominal concentration formulations in histidine and succinate at 200 mg/mL is within ±10% range.

Example 8: Assessment of Physical Properties at Elevated Temperatures

The following study was designed to assess the physical stability of high concentration anti-IL13 at a nominal concentration of 200 mg/mL upon exposure to thermal stress at suitably identified elevated temperature.

Samples were incubated at an elevated temperature of 50° C./60% RH for 7 or 10 days. Analytical testing included general appearance (GA), viscosity, concentration by A280 nm, SEC-HPLC, MFI and DLS. Table 19 summarizes the sample formulations used for the elevated temperature study.

TABLE 19

Formulations used for elevated temperature study

| Formulation# | mAb conc. (mg/mL) | Buffer system | pH | Surfactant (0.02%) | Viscosity modifier (150 mM) |
|---|---|---|---|---|---|
| 1 | 200 | 50 mM Acetate | 5.5 | PS80 | NaCl |
| 2 | 200 | 20 mM Succinate | 6.25 | PS80 | NaCl |
| 3 | 200 | 20 mM Histidine | 6.25 | PS80 | NaCl |

Figure 19:
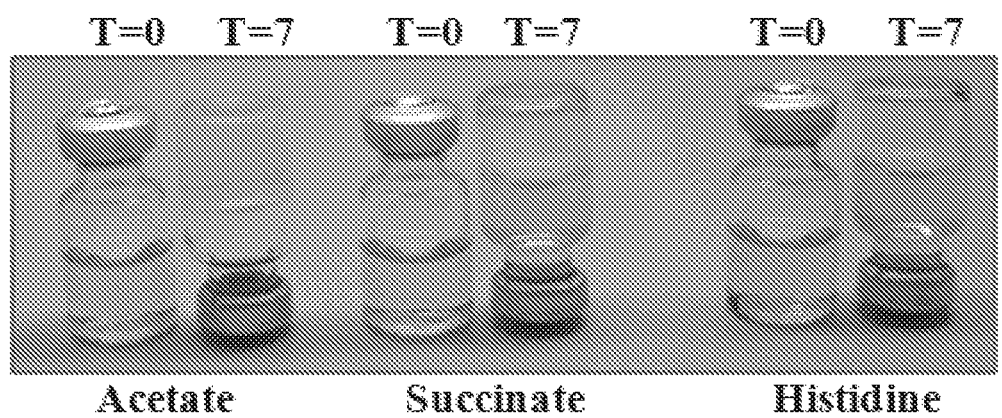
FIG. 19 shows that 7 day acetate samples were gelled (left). No gel was observed in the succinate or histidine samples (center and right). The 10 day succinate vial was observed to be in a semi-gel state.

The general appearance results, as summarized in Table 20 and FIG. 19, revealed gelation of formulation 1 (Acetate) after 7 days. Formulation 2 (Succinate) displayed semi-gelation after 10 days storage, while formulation 3 (Histidine) displayed no gelation of the sample after 10 days storage. No particles were observed in any of the samples which did not gel. The 7 days and 10 days succinate and histidine samples were classified as "milky iridescent." Milky iridescent equates to decrease in transparency which could be indicative of a higher concentration of subvisible particles and aggregation. MFI results (not shown) revealed t=0 of formulation 1 (Acetate) had ~50% more particles than other formulations.

TABLE 20

GA results for the planned 2 wk elevated temperature study at 50° C./60% RH

| Formulation | Time (days) | General Appearance (GA) |
|---|---|---|
| Formulation 1: Acetate | 0 | Opalescent |
| | 7 | Gel, milky iridescent |
| | 10 | Gel darker and more solid and opaque than 7 day gel |
| Formulation 2: Succinate | 0 | Opalescent |
| | 7 | Milky iridescent (more opalescent than initial) |
| | 10 | Semi-gel (gel could move within vial), milky |

TABLE 20-continued

GA results for the planned 2 wk elevated temperature study at 50° C./60% RH

| Formulation | Time (days) | General Appearance (GA) |
|---|---|---|
| Formulation 3: Histidine | 0 | Opalescent |
| | 7 | Milky iridescent |
| | 10 | Milky iridescent solution |

The results of the study clearly indicated the combination of 150 mM NaCl with histidine buffer at pH 6.25 prevented the gelation phenomena. The results also indicated that buffer type had a significant impact on physical stability (Histidine>Succinate>Acetate). These results may suggest a synergistic relationship which exists between the histidine buffer and NaCl to enhance the physical stability of high concentration mAb formulations.

Example 9: 200 mg/mL Freeze-Thaw Study

The purpose of this study was to evaluate the impact of three freeze-thaw cycles ranging between 2-8° C. and −70° C. on the physical and chemical stability profile of anti-IL13 mAb at a nominal concentration of 200 mg/mL. The freeze-thaw study examined stability in 15 mM histidine buffer pH 6.25, containing either 100 or 150 mM NaCl, 0.05 mm EDTA, 0.02% polysorbate 80. An acetate based formulation was included as a control at pH 5.5. The samples were filled at 1.2 mL fill volume into 3 mL glass vials and subjected to three freeze-cycles between 2-8° C. and −70° C., protected from light. Table 21 displays the samples for this study.

TABLE 21

Sample formulations tested for the freeze-thaw study

| Formulation | | |
|---|---|---|
| 200 mg/mL antiIL 13 in 15 mM Histidine pH 6.25 + 0.05 mM EDTA + 0.02% polysorbate 80 + 100 mM NaCl | A F/T -A | Control 3 Freeze/Thaw cycles |
| 200 mg/mL anti-IL13 in 15 mM Histidine pH 6.25 + 0.05 mM EDTA + 0.02% polysorbate 80 + 150 mM NaCl | B F/T -B | Control 3 Freeze/Thaw cycles |
| 200 mg/mL anti-IL13 in a acetate based formulation with various excipients at pH 5.5 | C F/T -C | Control 3 Freeze/Thaw cycles |

The samples were analyzed with the following analytical techniques: GA, pH, viscosity, concentration by A280 nm, potency by SPR, SDS-PAGE, SEC-HPLC, cIEF and MFI.

Freeze Thaw (F/T). There were no significant differences between results for F/T and control samples for any formulation by general appearance, pH, potency by SPR, concentration, SEC, SDS-PAGE or viscosity. There was no decrease in cIEF % Main from initial for the histidine formulations. Table 22 lists all the general appearance, pH, potency, concentration and viscosity data. Table 23 lists all the SDS-PAGE data. Table 24 lists all SEC and cIEF data. The overall results of the study clearly indicated the combination of 150 mM NaCl with histidine buffer at pH 6.25 was the best formulation and stable after being subjected to the freeze-thaw stress.

TABLE 22

Analytical testing results for freeze-thaw by GA, pH, potency, concentration and viscosity

| Sample Description | General Appearance | pH | Potency (Biacore) (mg/mL) | Concentration (mg/mL) | Viscosity (cps) |
|---|---|---|---|---|---|
| A | Opalescent, BY4, practically free from visible particles | 6.16 | 191.4 | 197.5 | 17.9 |
| F/T -A | Opalescent BY4, practically free from visible particles | 6.22 | 197.8 | 195.1 | 17.7 |
| B | Opalescent BY4, practically free from visible particles | 6.24 | 190.0 | 196.5 | 16.6 |
| F/T -B | Opalescent, BY4, practically free from visible particles | 6.24 | 197.3 | 201.0 | 16.6 |
| C | Opalescent, BY5, practically free from visible particles | 5.57 | 166.8 | 186.5 | 19.5 |
| F/T -C | Opalescent, BY5, practically free from visible particles | 5.57 | 171.3 | 199.1 | 18.9 |

TABLE 23

Freeze-Thaw Study Results (SDS-PAGE)

| Sample Description | Non reduced | | | Reduced | | |
|---|---|---|---|---|---|---|
| | % Main | % Agg | % Frag | % Heavy | % Light | % H + L |
| A | 82.8 | 0.8 | 10.7 | 64.8 | 32.3 | 97.1 |
| F/T -A | 82.4 | 0.6 | 11.1 | 65.6 | 31.2 | 96.8 |
| B | 83.6 | 0.7 | 10.3 | 65.0 | 31.5 | 96.6 |
| F/T -B | 83.6 | 0.6 | 10.4 | 65.8 | 31.0 | 96.8 |
| C | 80.1 | 1.1 | 12 | 63.3 | 32.0 | 95.2 |
| F/T -C | 78.8 | 1.2 | 12.9 | 63.9 | 31.5 | 95.4 |

TABLE 24

Freeze-Thaw Study Results (SEC, cIEF)

| Sample Description | SEC | | | cIEF | | | |
|---|---|---|---|---|---|---|---|
| | % Total Agg | % Monomer | % Frag | # bands | pI main | % Main | % Acidic | % Basic |
| A | 2.5 | 97.5 | 0.1 | 7 | 7.68 | 70.7 | 9.5 | 19.9 |
| F/T -A | 2.5 | 97.4 | 0.0 | 7 | 7.68 | 72.8 | 9.2 | 18.1 |
| B | 2.4 | 97.5 | 0.1 | 7 | 7.68 | 71.2 | 8.9 | 20.1 |
| F/T -B | 2.4 | 97.5 | 0.1 | 7 | 7.68 | 73.0 | 7.7 | 19.3 |
| C | 2.1 | 97.9 | 0.1 | 7 | 7.68 | 65.9 | 12.1 | 22.1 |
| F/T -C | 2.1 | 97.8 | 0.1 | 7 | 7.68 | 65.6 | 12.0 | 22.5 |

Example 10: Short Term Chemical Stability Study and Biophysical Characterization of a mAb Based Drug Product at a Nominal Concentration of 200 mg/mL A development stability study was performed to assess the short-term chemical stability of a 200 mg/mL mAb formulation containing NaCl, PS80 and EDTA. The short term chemical stability study examined stability in 15 mM histidine buffer pH 6.25, containing either 100 or 150 mM NaCl, 0.05 mm EDTA, 0.02% polysorbate 80. An acetate based formulation was included as a control. The samples were filled at 1.2 mL fill volume into 3 mL glass vials and placed at the following storage conditions 5° C., 25° C. and 40° C. Table 25 below displays the samples for this study.

TABLE 25

Short Term Chemical Stability Samples and initial osmolality results

| Formulations | Formula code | Osmolality (mOsm) |
|---|---|---|
| 200 mg/mL anti-IL13 in 15 mM Histidine pH 6.25 + 0.05 mM EDTA + 0.02% Polysorbate80 + 100 mM NaCl | A | 216 |
| 200 mg/mL anti-IL13 in 15 mM Histidine pH 6.25 + 0.05 mM EDTA + 0.02% Polysorbate80 + 150 mM NaCl | B | 333 |
| 200 mg/mL anti-IL13 in 50 mM acetate pH 5.5 + 51 mM NaCl + 0.05 mM EDTA + 1% arginine + 0.02% Polysorbate80 | C | 293 |

The samples were analyzed with the following analytical techniques: GA, pH viscosity, concentration by A280 nm, potency by SPR, SDS-PAGE, SEC-HPLC and cIEF. The study was for a total duration of 3 months and various biophysical characterization testing was also performed at initial and final time-point with DSC, DLS, CD and MFI.

Results from analytical (concentration, potency, SEC, SDS-PAGE, cIEF) and biophysical characterization (DSC, fluorescence, CD) testing indicate that formulation B (200 mg/mL anti-IL13 in 15 mM histidine, pH 6.25, 150 mM NaCl, 0.05 mM EDTA, 0.02% polysorbate 80) was the best of the three formulations for short term chemical stability.

Analytical Testing Results Summary and Discussion:

Table 26 summarizes 5° C. data up to 3 months by all the analytical techniques and Table 27 summarizes the stressed and accelerated data at 25° C. and 40° C. up to 3 months.

Samples in histidine formulations (A and B) exhibited higher % main after 3 months at 5° C. and 25° C. than the acetate control samples, as determined by cIEF. Purity determined by SDS-PAGE revealed higher % Heavy and Light chain content for samples in both histidine formulations (A and B) after 3 months at 25° C., than acetate control samples. At storage condition 40° C./75% RH, all three formulations after 1 month, exhibited a lower % H+L content compared to the initials, however formulations A and B surpassed formulation C (90.6 and 91.8 versus 88.2%). There were significant decreases in % Main for all 1 month 40° C. samples, but the decreases were smaller for the histidine formulations (8.8 or 7.5%) versus the change for acetate formulation (9.9%), with formulation B showing the lowest % decrease. Highest potency results were observed in histidine based formulation B containing 150 mM NaCl at the 3 months time-point at 25° C./60% RH and 1 month time point at 40° C./75% RH. Lowest potency was observed in the control and former acetate based formulation C which is not providing suitable stability for the high concentration mAb. Viscosity results for formulations A and B initial testing (18.0 and 16.3 cps) were lower than for formulation C (18.7 cps), as expected due to the higher NaCl concentration in formulations A and B (100 and 150 mM NaCl, respectively). Formulation B viscosity results were the lowest at all conditions and time points.

TABLE 26

5° C. Data for Short Term Chemical Stability

| Assay | Formulation Code | Initial | 1 m 5° C. | 3 m 5° C. | 16 m 5° C. |
|---|---|---|---|---|---|
| General Appearance | A | Opalescent, between B5 and B4, free from visible particles | Opalescent, BY4, practically free from visible particles | Opalescent, BY4, practically free from visible particles | Opalescent BY4, essentially free from visible particles |
| | B | Opalescent, between B5 and B4, free from visible particles | Opalescent, BY4, practically free from visible particles | Opalescent, BY4, practically free from visible particles | Opalescent. BY4, essentially free from visible particles |
| | C | Opalescent, between B5 and B4, free from visible particles | Opalescent, BY5, practically free from visible particles | Opalescent, BY5, practically free from visible particles | Opalescent, BY5, essentially free from visible particles |
| pH | A | 6.24 | 6.23 | 6.21 | 6.20 |
| | B | 6.26 | 6.24 | 6.24 | 6.19 |
| | C | 5.55 | 5.58 | 5.64 | 5.60 |
| Potency | A | 197.6 | 197.5 | 190.0 | NT |
| | B | 194.2 | 194.2 | 185.0 | NT |
| | C | 173.9 | 171.8 | 170.0 | NT |
| Concentration (mg/mL) | A | 202.6 | 196.12 | 195.0 | 196.2 |
| | B | 202.6 | 196.94 | 198.9 | 198.1 |
| | C | 208.2 | 190.46 | 185.7 | 199.4 |
| SDS-PAGE (% H + L, reduced) | A | NT | 97.5 | 97.0 | 97.9 |
| | B | NT | 97.6 | 97.0 | 97.7 |
| | C | NT | 96.2 | 96.0 | 96.0 |
| SEC % TotalAgg/ % Monomer/ % Fragment | A | 2.4  97.6  0.0 | 3.0  96.9  0.1 | 2.6  97.3  0.1 | 3.0  96.9  0.1 |
| | B | 2.3  97.7  0.0 | 3.0  96.9  0.1 | 2.5  97.4  0.1 | 3.0  96.9  0.1 |
| | C | 2.0  98.0  0.0 | 2.1  97.8  0.1 | 2.0  97.9  0.1 | 2.1  97.8  0.1 |

TABLE 26-continued

5° C. Data for Short Term Chemical Stability

| Assay | Formulation Code | Initial | | 1 m 5° C. | | 3 m 5° C. | | 16 m 5° C. | |
|---|---|---|---|---|---|---|---|---|---|
| cIEF | A | 7.67 | 70.9 | 7.68 | 71.4 | 7.68 | 73.4 | 7.68 | 73.6 |
| pI/% Main | B | 7.67 | 70.6 | 7.68 | 71.8 | 7.68 | 73.9 | 7.68 | 73.6 |
| | C | 7.68 | 63.7 | 7.68 | 65.0 | 7.68 | 66.5 | 7.68 | 67.4 |
| Viscosity | A | | 18.0 | | 17.6 | | 18.4 | | 15.87 |
| (cps) | B | | 16.3 | | 16.3 | | 17.0 | | 14.85 |
| | C | | 18.7 | | 18.5 | | 18.8 | | 16.41 |

TABLE 27

Stressed and Accelerated Data for Short Term Chemical Stability

| Assay | Formulation Code | Initial | | | 1 m 40° C. | | | 3 m 25° C. | | |
|---|---|---|---|---|---|---|---|---|---|---|
| General Appearance | A | Opalescent, between B5 and 84, free from visible particles | | | Opalescent, BY4, practically free from visible particles | | | Opalescent, BY4, practically free from visible particles | | |
| | B | Opalescent, between B5 and B4, free from visible particles | | | Opalescent, BY4, practically free from visible particles | | | Opalescent, BY4, practically free from visible particles | | |
| | C | Opalescent, between B5 and B4, free from visible particles | | | Opalescent BY5, practically free from visible particles | | | Opalescent, BY5, practically free from visible particles | | |
| pH | A | | 6.24 | | | 6.18 | | | 6.20 | |
| | B | | 6.26 | | | 6.22 | | | 6.22 | |
| | C | | 5.55 | | | 5.51 | | | 5.66 | |
| Potency | A | | 197.6 | | | 138.1 | | | 167.0 | |
| | B | | 194.2 | | | 149.0 | | | 176.0 | |
| | C | | 173.9 | | | 124.8 | | | 146.0 | |
| Concentration | A | | 202.6 | | | 195.12 | | | 185.1 | |
| (mg/mL) | B | | 202.6 | | | 199.04 | | | 195.1 | |
| | C | | 208.2 | | | 187.39 | | | 200.3 | |
| SDS-PAGE | A | | NT | | | 90.6 | | | 95.7 | |
| (% H + L, reduced) | B | | NT | | | 91.8 | | | 95.3 | |
| | C | | NT | | | 88.2 | | | 93.1 | |
| SEC % TotalAgg/ | A | 2.4 | 97.6 | 0.0 | 5.3 | 92.9 | 1.8 | 3.6 | 94.7 | 1.7 |
| % Monomer/ | B | 2.3 | 97.7 | 0.0 | 5.2 | 93.1 | 1.7 | 3.6 | 94.9 | 1.5 |
| % Fragment | C | 2.0 | 98.0 | 0.0 | 4.8 | 93.5 | 1.8 | 2.6 | 95.6 | 1.9 |
| cIEF | A | 7.67 | 70.9 | | 7.68 | 62.1 | | 7.68 | 70.9 | |
| pI/% Main | B | 7.67 | 70.6 | | 7.68 | 63.1 | | 7.68 | 69.8 | |
| | C | 7.67 | 63.7 | | 7.68 | 53.8 | | 7.68 | 60.6 | |
| Viscosity | A | | 18.0 | | | 18.2 | | | 19.1 | |
| (cps) | B | | 16.3 | | | 17.2 | | | 16.5 | |
| | C | | 18.7 | | | 20.0 | | | 19.3 | |

Figure 20:
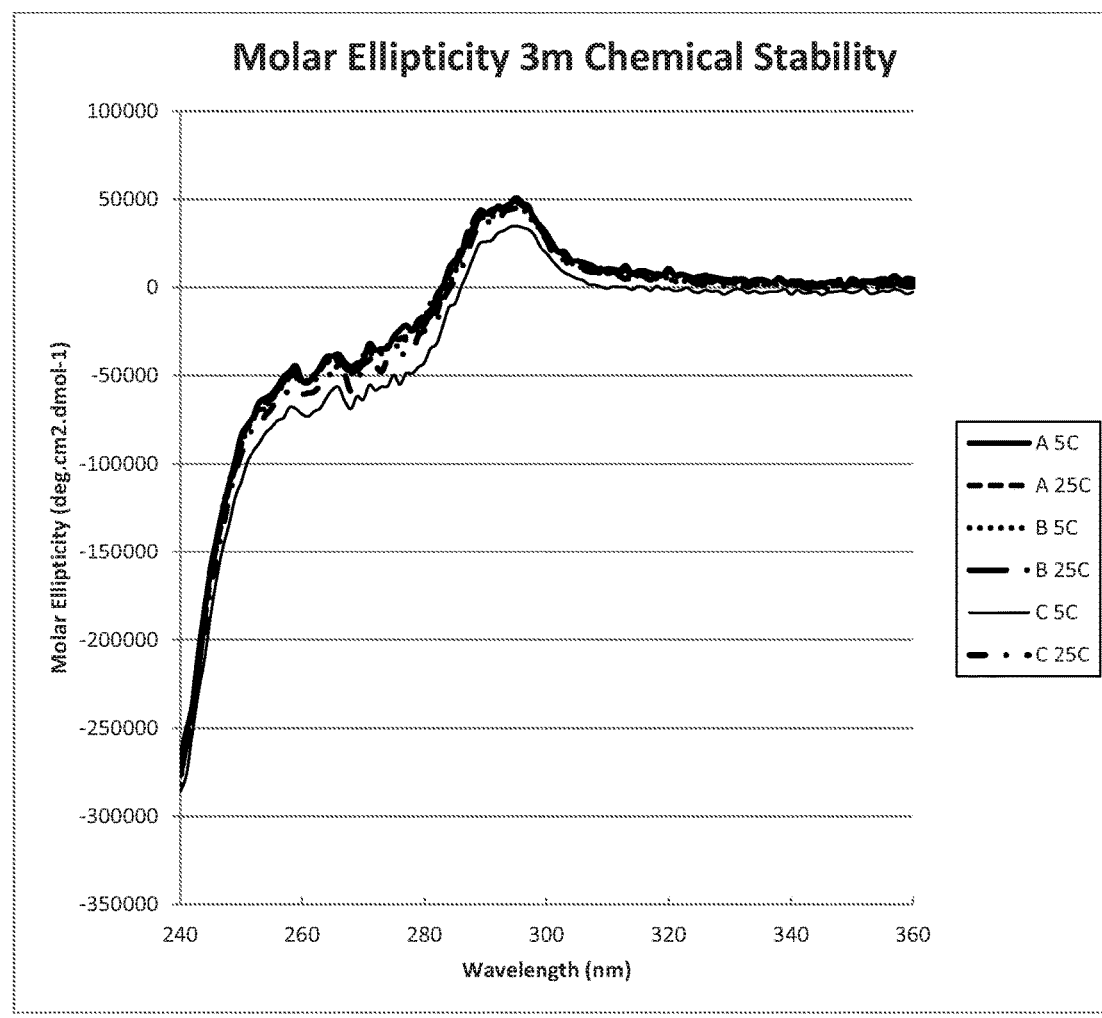
FIG. 20 shows a comparison of near-UV circular dichroism spectra for 3 month chemical stability samples.

Biophysical Characterization Results Summary and Discussion:

Table 28 shows DLS data for initial and Fluorescence data for initial and 3 months.
MFI results displayed no visible particles were observed in any sample over 3 months. No significant differences were observed among the three formulations by DLS, which measure the hydrodynamic radii of the mAb. Fluorescence and circular dichroism data did not indicate perturbations to the secondary and tertiary structure in histidine formulations after 3 months storage. FIG. 20 displays the CD comparison plot of the spectra. The lower signal for formulation C samples could indicate a change in the tertiary structure. The differences seen in % quench for formulation C also indicate a change in tertiary structure for this formulation. The DSC data for initial and 3 month samples are displayed in Table 29. The trend of higher Tm and total kcal/mole results for both histidine/NaCl formulations suggests that the additional salt allows for greater thermodynamic stability than the acetate formulation.

TABLE 28

DLS and Fluorescence Data for Short Term Chemical Stability

| | | DLS | Fluorescence | | |
|---|---|---|---|---|---|
| Sample | Condition | Rh (nm) | max (nm) | F.I. at max (absorbance) | Quenching (%) |
| A | Initial | 5.5 | 340 | 402 | n/a |
| B | Initial | 5.5 | 342 | 451 | n/a |
| C | Initial | 5.7 | 341 | 365 | n/a |
| A | 3 m 5° C. | NT | 341 | 418 | 4.0 |
| B | 3 m 5° C. | NT | 341 | 454 | 0.7 |
| C | 3 m 5° C. | NT | 342 | 466 | 27.7 |
| A | 3 m 25° C. | NT | 341 | 352 | −12.4 |
| B | 3 m 25° C. | NT | 341 | 407 | −9.8 |
| C | 3 m 25° C. | NT | 342 | 452 | 23.8 |
| A | 16 m 5° C. | NT | 340 | 355 | −11.7 |
| B | 16 m 5° C. | NT | 341 | 402 | −10.9 |
| C | 16 m 5° C. | NT | 342 | 436 | 19.5 |

TABLE 29

DSC Data for Short Term Chemical Stability

| Formula | Code | Tm1 (° C.) | Tm2 (° C.) | Tm3 (° C.) | Total area kcal/mole |
|---|---|---|---|---|---|
| A | Initial | 68.7 | 74.0 | 82.8 | 960 |
| A | 3 m 5° C. | 68.6 | 74.0 | 82.8 | 988 |
| A | 3 m 25° C. | 68.5 | 74.5 | 82.9 | 1122 |
| A | 16 m 5° C. | 68.8 | 74.3 | 82.8 | 902 |
| B | Initial | 68.4 | 73.4 | 82.7 | 1036 |
| B | 3 m 5° C. | 68.4 | 73.4 | 82.6 | 965 |
| B | 3 m 25° C. | 68.3 | 73.8 | 82.7 | 1055 |
| B | 16 m 5° C. | 68.4 | 73.5 | 82.6 | 1081 |
| C | Initial | 67.9 | 73.1 | 82.9 | 884 |
| C | 3 m 5° C. | 67.7 | 73.1 | 82.9 | 891 |
| C | 3 m 25° C. | 67.7 | 73.6 | 83.0 | 947 |
| C | 16 m 5° C. | 67.7 | 73.2 | 82.8 | 928 |

Example 11: Long Term Chemical Stability Study and Biophysical Characterization of a mAb Based Drug Product at a Nominal Concentration of 200 mg/mL A 16-month time-point was tested for all samples on stability as listed in Table 26. The results of this time point was used to assess the long-term chemical stability of the mAb drug product at a nominal concentration of 200 mg/mL formulated in His, NaCl, PS80 and EDTA. Limited testing was performed to confirm the long-term stability.

The samples were analyzed with the following analytical techniques: GA, pH, viscosity, concentration by A280 nm, SDS-PAGE, SEC-HPLC and cIEF. Biophysical characterization testing was also performed which included fluorescence, DSC and CD.

Table 26 includes 5° C. data at the 16 months time-point by all the analytical techniques.

Analytical testing results summary and discussion: Samples in histidine formulations (A and B) exhibited higher % Monomer content after 16 months at 5° C. Formulation C was 0.9% higher than either of the histidine formulations.

Biophysical characterization results summary and discussion: Overall, biophysical characterization results were comparable between the 3 month and the 16 months time-point. Fluorescence and circular dichroism data did not indicate perturbations to the secondary and tertiary structure in histidine formulations after 16 months storage. The results for 16 month formulation A and B samples at 5° C. show no significant changes. There were significant intensity increases for both formulation C samples, which indicates that the molecule is unfolding and exposing more fluorescent groups. There was no increase in visible particles at 16 month time point based on analysis by MFI results for formulations A and B. The DSC data for samples at 16 months time point. The trend of higher Tm and total kcal/mole results for both histidine/NaCl formulations suggests that the additional salt allows for greater thermodynamic stability than the acetate formulation.

Table 28 shows Fluorescence data for 16 month time-point. Table 29 shows the DSC results for the 16 month time-point.

Results from analytical (concentration, potency, SEC, SDS-PAGE, cIEF) and biophysical characterization (DSC, fluorescence, CD) testing indicate that Formulation A (200 mg/mL anti-IL13 in 15 mM histidine, pH 6.25, 150 mM NaCl, 0.05 mM EDTA, 0.02% polysorbate 80) was the best of the three formulations for long term chemical stability.

```
                    Sequence Listing

BLyS                                       SEQ ID NO: 1
MDDSTEREQS RLTSCLKKRE EMKLKECVSI LPRKESPSVR

SSKDGKLLAA TLLLALLSCC LTVVSFYQVA ALQGDLASLR

AELQGHHAEK LPAGAGAPKA GLEEAPAVTA GLKIFEPPAP

GEGNSSQNSR NKRAVOGPEE TVTQDCLQLI ADSETPTIQK

GSYTFVPWLL SFKRGSALEE YENKTLVYET GYFFIYGQVL

YTDKTYAMGH LIQRKEVBVF GDELSLVTLF RCIQNMPETL

PNNSCYSAGI AKLEEGDELQ LAIPRENAQI SLDGDVTFFG

ALKLL

Belimumab VH                               SEQ ID NO: 2
QVQLQQSGAE VKKPGSSVRV SCKASGGTFN NNAINWVRQA

PGQGLEWMGG IIPMFGTAKY SQNFQGRVAI TADESTGTAS

MELSSLRSED TAVYYCARSR DLLLFPHHAL SPWGRGTMVT

VSS

Belimumab VL                               SEQ ID NO: 3
SSELTODPAV SVALGQTVRV TCQGDSLRSY YASWYQQKPG

QAPVLVIYGK NNRPSGIPDR FSGSSSGNTA SLTITGAQAE

DEADYYCSSR DSSGNHWVEG GGTELTVLG

Tabalumab VH                               SEQ ID NO: 4
MKHLWFFLLL VAAPRWVLSQ VQLQQWGAGL LKPSETLSLT

CAVYGGSFSG YYWSWIRQPP GKGLEWIGEI NHSGSTNYNP

SLKSRVTISV DTSKNQFSLK LSSVTAADTA VYYCARGYYD

ILTGYYYFD YWGQGTLVTV SS

Tabalumab VL                               SEQ ID NO: 5
EIVLTQSPAT LSLSPGERAT LSCRASQSVS RYLAWYQQKP

GQAPRLLIYD ASNRATGTPA RFSGSGSGTD STLTISSLEP

EDFAVYYCQQ RSNWPRTFGQ GTKVEIKRT

Belimumab heavy chain                      SEQ ID NO: 6
QVQLOQSGAE VKKPGSSVRV SCKASGGTFN NNAINWVRQA

PGQGLEWMGG IIPMFGTAKY SQNFQGRVAI TADESTGTAS

MELSSLRSED TAVYYCARSR DLLLFPHHAL SPWGRGTMVT

VSSASTKGPS VFPLAPSSKS TSGGTAALGC LVKDYFPEPV

TVSWNSGALT SGVHTFPAVL QSSGLYSLSS VVTVPSSSLG

TQTYICNVNH KPSNTKVDKK VEPKSCDKTH TCPPCPAPEL

LGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

RDELTKNQVS LTCLVKGFYP SDIAVEWESN GQPENNYKTT
```

Sequence Listing

PPVLDSDGSF FLYSKLTVDK SRWQQGNVFS CSVMBEALHN
HYTQKSLSLS PGS

Belimumab light chain                    SEQ ID NO: 7
SSELTQDPAV SVALGQTVRV TCQGDSLRSY YASWYQQKPG
QAPVLVTYGK NNRPSGIPDR FSGSSSGNTA SLTITGAQAE
DEADYYCSSR DSSGNHWVFG GGTELTVLGQ PKAAPSVTLF
PPSSEELQAN KATLVCLISD FYPGAVTVAW KADSSPVKAG
VETTTPSKQS NNKYAASSYL SLTPEQWKSH RSYSCQVTHE
GSTVEKTVAP TECS Tabalumab heavy chain                    SEQ ID NO: 8
QVQLQQWGAG LLYPSETLSL TCAVYGGSFS GYYWGWIRQP
PGKGLEWIGE INHSGSTNYN PSLKSRVTIS VDTSKNQFSL
KLSSVTAADT AVYYCARGYY DILTGYYYF DYWGQGTLVT
VSSASTKGPS VFPLAPCSRS TSESTAALGC LVKDYFPEPV
TVSWNSGALT SGVHTFPAVL QSSGLYSLSS VVTVPSSSLG
TKTYTCNVDH KPSOTKVDKR VESKYGPPCP PCPAPEFLGG
PSVFLFPPKP KDTLMISRTP EVTCVVVDVS QEDPEVQFNW
YVDGVEVHNA KTKPREEQFN STYRVVSVLT VLHQDWLNGK
EYKCKVSNKG LPSSIEKTIS KAKGQPREPQ VYTLPPSQEE
MTKNQVSLTC LVKGFYPSDI AVEWESNGQP ENNYKTTPPV
LDSDGSFFLY SRLTVDKSRW QEGNVFSCSV MHEALHNHYT
QKSISISLGK Tabalumab light chain                    SEQ ID NO: 9
EIVLTQSPAT LSLSPGERAT LSCRASQSVS RYLAWYQQKP
GQAPRLLIYD ASNRATGIPA RFSGSGSGTD STLTISSLEP
EDFAVYYCQQ RSNWPRTFGQ GTKVEIKRTV AAPSVFIFPP
SDEQLKSGTA SVVCLLNNFY PREAKVQWKV DNALQSGNSQ
ESVTEQDSKD STYSLSNTLT LSKADYEKHK VYACEVTHQG
LSSPVTKSFN RGES Soluble Form of BLyS                     SEQ ID NO: 10
AVQGPEETVT QDCLQLIADS ETPTIQKGSY TFVPWILSFK
RGSALEEKEN KILVKETGYF FIYGQVLYTD KTYAMGHLIQ
REKVHVEGDE LSLVTLFRCI QNMPETLPNN SCYSAGIAKL
EEGDELQLAI PRENAQISLD GDVTFFGALK LL Belimumab CDRH1                          SEQ ID NO: 11
GGTFNNNAIN Belimumab CDRH2                          SEQ ID NO: 12
GIIPMFGTAK YSQNFQG Belimumab CDRH3                          SEQ ID NO: 13
SRDLLLFPHH ALSP Belimumab CDRL1                          SEQ ID NO: 14
QGDSLRSYYA S Belimumab CDRL2                          SEQ ID NO: 15
GKNNRPS Belimumab CDRL3                          SEQ ID NO: 16
SSRDSSGNHW V

---

We claim:

1. A pharmaceutical formulation for an antigen binding protein comprising:
   a. 200±20 mg/mL of the antigen binding protein;
   b. about 5-15 mM of a buffering agent which is histidine providing a pH of 6.0±0.5;
   c. about 115+10 mM of a tonicity agent which is sodium chloride;
   d. about 20-30 mM of a stabilizer which is arginine; and
   e. about 0.005 to 0.015% (w/v) of a nonionic surfactant which is polysorbate 80;
   wherein the antigen binding protein comprises amino acid sequences CDRH1 of SEQ ID NO:11, CDRH2 of SEQ ID NO: 12, CDRH3 of SEQ ID NO:13, CDRL1 of SEQ ID NO:14, CDRL2 of SEQ ID NO:15, and CDRL3 of SEQ ID NO:16.

2. The pharmaceutical formulation according to claim 1, wherein said antigen binding protein is a monoclonal antibody or fragment thereof.

3. The pharmaceutical formulation according to claim 2, wherein said monoclonal antibody or fragment thereof binds to BLyS (SEQ ID NO: 1) or a hetero- or homo-trimeric form of BLyS.

4. The pharmaceutical formulation according to claim 2, wherein said antigen binding protein is a monoclonal antibody and the monoclonal antibody comprises heavy and light chain variable regions comprising amino acid sequences that are 90%, 91%, 92%, 93%, 94%, 95%, 96%, 97%, 98%, or 99% identical to SEQ ID NOs: 2 and 3, respectively.

5. The pharmaceutical formulation according to claim 2, wherein said antigen binding protein is a monoclonal antibody and the monoclonal antibody comprises heavy and light chains comprising amino acid sequences that are 90%, 91%, 92%, 93%, 94%, 95%, 96%, 97%, 98%, or 99% identical to SEQ ID NOs: 6 and 7, respectively.

6. The pharmaceutical formulation according to claim 2, wherein the antigen binding protein is a monoclonal antibody and the monoclonal antibody concentration is about 200 mg/mL.

7. The pharmaceutical formulation according to claim 2, wherein the histidine concentration is 10±2 mM.

8. The pharmaceutical formulation according to claim 2, wherein the arginine concentration is 25±2 mM.

9. The pharmaceutical formulation according to claim 2, wherein the polysorbate 80 concentration is about 0.01% (w/v).

10. The pharmaceutical formulation according to claim 2 which is stable upon freezing and thawing.

11. The pharmaceutical formulation according to claim 2 for subcutaneous or intramuscular administration.

12. A method of treating a disease or condition which is amenable to treatment with an anti-BLyS antibody in a human comprising administering to said human the pharmaceutical formulation according to claim 2, wherein said disease or condition is selected from the group consisting of systemic lupus erythematosus, anti-neutrophil cytoplasmic antibody vasculitis, lupus nephritis, primary Sjögren's syndrome, chronic immune thrombocytopenia, myasthenia gravis, symptomatic Waldenström's macroglobulinaemia, immune desensitizing of patients awaiting kidney transplant, membranous nephropathy, systemic sclerosis, rheumatoid arthritis, multiple myeloma, multiple sclerosis, and kidney failure.

13. The method according to claim 12, wherein the disease or condition is systemic lupus erythematosus.

14. The method according to claim 12, wherein the disease or condition is primary Sjögren's syndrome.

15. The pharmaceutical formulation according to claim 2, wherein said antigen binding protein is a monoclonal antibody and the monoclonal antibody comprises heavy and light chains comprising amino acid sequences that are identical to SEQ ID NOs: 6 and 7, respectively.

16. The pharmaceutical formulation according to claim 4, wherein the histidine is L-histidine.

17. A pharmaceutical formulation for a monoclonal antibody comprising:
  a. 200±20 mg/mL of the monoclonal antibody;
  b. about 5-15 mM of a buffering agent which is histidine providing a pH of 6.0±0.5;
  c. about 115+10 mM of a tonicity agent which is sodium chloride;
  d. about 20-30 mM of a stabilizer which is arginine; and
  e. about 0.005 to 0.015% (w/v) of a nonionic surfactant which is polysorbate 80;
  wherein the monoclonal antibody comprises a heavy chain variable region comprising the amino acid sequence of SEQ ID NO:2 and a light chain variable region comprising the amino acid sequence of SEQ ID NO:3.

18. The pharmaceutical formulation according to claim 17, wherein the histidine is L-histidine.

19. A method of treating systemic lupus erythematosus in a human comprising administering to the human a pharmaceutical composition comprising:
  a. 200±20 mg/mL of a monoclonal antibody;
  b. about 5-15 mM of a buffering agent which is histidine providing a pH of 6.0±0.5;
  c. about 115+10 mM of a tonicity agent which is sodium chloride;
  d. about 20-30 mM of a stabilizer which is arginine; and
  e. about 0.005 to 0.015% (w/v) of a nonionic surfactant which is polysorbate 80;
  wherein the monoclonal antibody comprises a heavy chain variable region comprising the amino acid sequence of SEQ ID NO:2 and a light chain variable region comprising the amino acid sequence of SEQ ID NO:3.

20. The method of claim 19, wherein the histidine is L-histidine.

21. A method of treating primary Sjögren's syndrome in a human comprising administering to the human a pharmaceutical composition comprising:
  a. 200±20 mg/mL of a monoclonal antibody;
  b. about 5-15 mM of a buffering agent which is histidine providing a pH of 6.0±0.5;
  c. about 115+10 mM of a tonicity agent which is sodium chloride;
  d. about 20-30 mM of a stabilizer which is arginine; and
  e. about 0.005 to 0.015% (w/v) of a nonionic surfactant which is polysorbate 80;
  wherein the monoclonal antibody comprises a heavy chain variable region comprising the amino acid sequence of SEQ ID NO:2 and a light chain variable region comprising the amino acid sequence of SEQ ID NO:3.

22. The method of claim 21, wherein the histidine is L-histidine.

23. A pharmaceutical formulation for an antigen binding protein comprising:
  a. 200 mg/mL of the antigen binding protein;
  b. 10 mM of L-histidine;
  c. 115 mM of sodium chloride;
  d. 25 mM of L-arginine hydrochloride; and
  e. 0.01% (w/v) of polysorbate 80;
wherein the antigen binding protein comprises amino acid sequences CDRH1 of SEQ ID NO:11, CDRH2 of SEQ ID NO: 12, CDRH3 of SEQ ID NO:13, CDRL1 of SEQ ID NO:14, CDRL2 of SEQ ID NO:15, and CDRL3 of SEQ ID NO:16, and wherein the antigen binding protein is a monoclonal antibody or fragment thereof.

24. The pharmaceutical formulation according to claim 23 which is stable upon freezing and thawing.

25. The pharmaceutical formulation according to claim 23 for subcutaneous or intramuscular administration.

* * * * *

SEQUENCE LISTING

<160> NUMBER OF SEQ ID NOS: 16

<210> SEQ ID NO 1
<211> LENGTH: 285
<212> TYPE: PRT
<213> ORGANISM: Artificial Sequence
<220> FEATURE:
<223> OTHER INFORMATION: BLyS
<220> FEATURE:
<223> OTHER INFORMATION: Amino Acid Sequence identified using molecular
      biology techniques.

<400> SEQUENCE: 1

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

```
Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 2
<211> LENGTH: 123
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 2

Gln Val Gln Leu Gln Gln Ser Gly Ala Glu Val Lys Lys Pro Gly Ser
1               5                   10                  15

Ser Val Arg Val Ser Cys Lys Ala Ser Gly Gly Thr Phe Asn Asn Asn
            20                  25                  30

Ala Ile Asn Trp Val Arg Gln Ala Pro Gly Gln Gly Leu Glu Trp Met
        35                  40                  45

Gly Gly Ile Ile Pro Met Phe Gly Thr Ala Lys Tyr Ser Gln Asn Phe
    50                  55                  60

Gln Gly Arg Val Ala Ile Thr Ala Asp Glu Ser Thr Gly Thr Ala Ser
65                  70                  75                  80

Met Glu Leu Ser Ser Leu Arg Ser Glu Asp Thr Ala Val Tyr Tyr Cys
                85                  90                  95

Ala Arg Ser Arg Asp Leu Leu Leu Phe Pro His His Ala Leu Ser Pro
            100                 105                 110

Trp Gly Arg Gly Thr Met Val Thr Val Ser Ser
        115                 120

<210> SEQ ID NO 3
<211> LENGTH: 109
<212> TYPE: PRT
<213> ORGANISM: Artificial Sequence
```

```
<220> FEATURE:
<223> OTHER INFORMATION: Amino Acid Sequence identified using molecular
      biology techniques.

<400> SEQUENCE: 3

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly
            100                 105

<210> SEQ ID NO 4
<211> LENGTH: 142
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 4

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Gly Tyr Tyr Asp Ile Leu Thr Gly Tyr Tyr Tyr Tyr
        115                 120                 125

Phe Asp Tyr Trp Gly Gln Gly Thr Leu Val Thr Val Ser Ser
130                 135                 140

<210> SEQ ID NO 5
<211> LENGTH: 109
<212> TYPE: PRT
<213> ORGANISM: Artificial Sequence
<220> FEATURE:
<223> OTHER INFORMATION: Amino Acid Sequence identified using molecular
      biology techniques.
```

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr
            100                 105

<210> SEQ ID NO 6
<211> LENGTH: 453
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 6

Gln Val Gln Leu Gln Gln Ser Gly Ala Glu Val Lys Lys Pro Gly Ser
1               5                   10                  15

Ser Val Arg Val Ser Cys Lys Ala Ser Gly Gly Thr Phe Asn Asn Asn
            20                  25                  30

Ala Ile Asn Trp Val Arg Gln Ala Pro Gly Gln Gly Leu Glu Trp Met
        35                  40                  45

Gly Gly Ile Ile Pro Met Phe Gly Thr Ala Lys Tyr Ser Gln Asn Phe
50                  55                  60

Gln Gly Arg Val Ala Ile Thr Ala Asp Glu Ser Thr Gly Thr Ala Ser
65                  70                  75                  80

Met Glu Leu Ser Ser Leu Arg Ser Glu Asp Thr Ala Val Tyr Tyr Cys
                85                  90                  95

Ala Arg Ser Arg Asp Leu Leu Leu Phe Pro His His Ala Leu Ser Pro
            100                 105                 110

Trp Gly Arg Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 7
<211> LENGTH: 214
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 7

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140
```

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210

<210> SEQ ID NO 8
<211> LENGTH: 450
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 8

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ile Leu Thr Gly Tyr Tyr Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Gln Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285
```

```
Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 9
<211> LENGTH: 214
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 10
<211> LENGTH: 152
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 10

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
    50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
    130                 135                 140

Phe Phe Gly Ala Leu Lys Leu Leu
145                 150

<210> SEQ ID NO 11
<211> LENGTH: 10
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 11

Gly Gly Thr Phe Asn Asn Asn Ala Ile Asn
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 12

Gly Ile Ile Pro Met Phe Gly Thr Ala Lys Tyr Ser Gln Asn Phe Gln
1               5                   10                  15

Gly
```

```
<210> SEQ ID NO 13
<211> LENGTH: 14
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 13

Ser Arg Asp Leu Leu Leu Phe Pro His His Ala Leu Ser Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 14

Gln Gly Asp Ser Leu Arg Ser Tyr Tyr Ala Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 15

Gly Lys Asn Asn Arg Pro Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Amino Acid Sequence identified using molecular
      biology techniques.

<400> SEQUENCE: 16

Ser Ser Arg Asp Ser Ser Gly Asn His Trp Val
1               5                   10
```